US008642063B2

(12) United States Patent
Sarasam et al.

(10) Patent No.: US 8,642,063 B2
(45) Date of Patent: *Feb. 4, 2014

(54) IMPLANTABLE MEDICAL DEVICE COATINGS WITH BIODEGRADABLE ELASTOMER AND RELEASABLE TAXANE AGENT

(75) Inventors: Aparna Reddy Sarasam, West Lafayette, IN (US); Angela Rose Barnett, Lafayette, IN (US); Krista Nicole Gearhart, Lafayette, IN (US); Jason Lichti, West Lafayette, IN (US); Priscilla Reyes, Duncan, OK (US)

(73) Assignee: Cook Medical Technologies LLC, Bloomington, IN (US)

( * ) Notice: Subject to any disclaimer, the term of this patent is extended or adjusted under 35 U.S.C. 154(b) by 1070 days.

This patent is subject to a terminal disclaimer.

(21) Appl. No.: 12/544,281

(22) Filed: Aug. 20, 2009

(65) Prior Publication Data

US 2010/0049296 A1 Feb. 25, 2010

Related U.S. Application Data

(60) Provisional application No. 61/091,045, filed on Aug. 22, 2008.

(51) Int. Cl.
*A61F 2/00* (2006.01)
*A61F 2/02* (2006.01)
*A61K 31/337* (2006.01)

(52) U.S. Cl.
USPC ............ 424/423; 424/422; 604/500; 623/1.1; 514/449

(58) Field of Classification Search
None
See application file for complete search history.

(56) References Cited

U.S. PATENT DOCUMENTS

| | | | |
|---|---|---|---|
| 4,795,475 A | 1/1989 | Walker | 623/66 |
| 4,814,470 A | 3/1989 | Colin et al. | 514/449 |
| 4,857,653 A | 8/1989 | Colin et al. | 549/511 |
| 4,942,184 A | 7/1990 | Haugwitz et al. | 51/449 |
| 5,002,583 A | 3/1991 | Pitaru et al. | 623/66 |
| 5,059,699 A | 10/1991 | Kingston et al. | 549/511 |
| 5,200,534 A | 4/1993 | Rao | 549/510 |
| 5,202,448 A | 4/1993 | Carver et al. | 549/510 |
| 5,213,580 A | 5/1993 | Slepian et al. | 623/1 |

(Continued)

FOREIGN PATENT DOCUMENTS

| | | | |
|---|---|---|---|
| EP | 0590 267 A2 | 4/1994 | C07D 305/14 |
| WO | WO 93/10076 A1 | 5/1993 | C07C 231/20 |

(Continued)

OTHER PUBLICATIONS

Liggins et al. Solid-state characterization of paclitaxel. J. Pharmaceutical Sciences, 1997, vol. 86, No. 12, pp. 1458-1463.*

(Continued)

*Primary Examiner* — Lakshmi Channavajjala
(74) *Attorney, Agent, or Firm* — Brinks Gilson & Lione

(57) ABSTRACT

A coated medical device, such as a stent, that elutes a taxane agent in a controlled manner is provided. In one embodiment, the taxane agent is paclitaxel and at least a portion of the paclitaxel is present in a dihydrate solid form. The medical device may be coated with a layer including a taxane agent and a layer of bioabsorbable elastomer over the layer including the taxane agent. Methods of manufacturing and using the coated medical device are also provided.

20 Claims, 8 Drawing Sheets

(56) References Cited

U.S. PATENT DOCUMENTS

| | | | |
|---|---|---|---|
| 5,229,529 A | 7/1993 | Ueno et al. | 549/305 |
| 5,248,796 A | 9/1993 | Chen et al. | 549/510 |
| 5,254,580 A | 10/1993 | Chen et al. | 514/449 |
| 5,272,171 A | 12/1993 | Ueda et al. | 514/449 |
| 5,274,137 A | 12/1993 | Nicolaou et al. | 549/510 |
| 5,278,324 A | 1/1994 | Kingston et al. | 549/510 |
| 5,279,949 A | 1/1994 | Nair | 435/123 |
| 5,283,253 A | 2/1994 | Holton et al. | 514/444 |
| 5,294,637 A | 3/1994 | Chen et al. | 514/449 |
| 5,300,638 A | 4/1994 | Farina et al. | 540/357 |
| 5,342,348 A | 8/1994 | Kaplan | 604/891.1 |
| 5,350,866 A | 9/1994 | Holton et al. | 549/510 |
| 5,352,805 A | 10/1994 | Kingston et al. | 549/510 |
| 5,362,831 A | 11/1994 | Mongelli et al. | 526/304 |
| 5,380,751 A | 1/1995 | Chen et al. | 514/449 |
| 5,395,850 A | 3/1995 | Roth | 514/471 |
| 5,411,984 A | 5/1995 | Kingston et al. | 514/449 |
| 5,412,092 A | 5/1995 | Rey et al. | 540/200 |
| 5,422,364 A | 6/1995 | Nicolaou et al. | 514/449 |
| 5,440,056 A | 8/1995 | Klein et al. | 549/510 |
| 5,443,458 A | 8/1995 | Eury | 604/891.1 |
| 5,447,724 A | 9/1995 | Helmus et al. | 424/426 |
| 5,464,650 A | 11/1995 | Berg et al. | 427/2.3 |
| 5,591,227 A | 1/1997 | Dinh et al. | 623/1 |
| 5,599,352 A | 2/1997 | Dinh et al. | 623/1 |
| 5,605,696 A | 2/1997 | Eury et al. | 424/423 |
| 5,624,411 A | 4/1997 | Tuch | 604/265 |
| 5,629,077 A | 5/1997 | Turnlund et al. | 442/38 |
| 5,649,977 A | 7/1997 | Campbell | 623/1 |
| 5,697,967 A | 12/1997 | Dinh et al. | 623/1 |
| 5,741,323 A | 4/1998 | Pathak et al. | 623/1 |
| 5,749,922 A | 5/1998 | Slepian et al. | 623/1 |
| 5,766,710 A | 6/1998 | Turnlund et al. | 428/36.1 |
| 5,773,019 A | 6/1998 | Ashton et al. | 424/423 |
| 5,776,184 A | 7/1998 | Tuch | 623/1 |
| 5,788,979 A | 8/1998 | Alt et al. | 424/426 |
| 5,824,048 A | 10/1998 | Tuch | 623/1 |
| 5,837,008 A | 11/1998 | Berg et al. | 623/1 |
| 5,876,743 A | 3/1999 | Ibsen et al. | 424/426 |
| 5,957,975 A | 9/1999 | Lafont et al. | 623/1 |
| 5,980,551 A | 11/1999 | Summers et al. | 606/194 |
| 6,001,386 A | 12/1999 | Ashton et al. | 424/423 |
| 6,153,252 A | 11/2000 | Hossainy et al. | 427/2.3 |
| 6,240,616 B1 | 6/2001 | Yan | 29/527.2 |
| 6,258,121 B1 | 7/2001 | Yang et al. | 623/1.46 |
| 6,268,390 B1 | 7/2001 | Kunz | 514/411 |
| 6,299,604 B1 | 10/2001 | Ragheb et al. | 604/265 |
| 6,306,426 B1 | 10/2001 | Olejnik et al. | 424/426 |
| 6,333,347 B1 | 12/2001 | Hunter et al. | 514/449 |
| 6,395,023 B1 | 5/2002 | Summers | 623/1.44 |
| 6,451,373 B1 | 9/2002 | Hossainy et al. | 427/2.25 |
| 6,468,304 B1 | 10/2002 | Dubois-Rande et al. | 623/1.42 |
| 6,471,979 B2 | 10/2002 | New et al. | 424/422 |
| 6,485,514 B1 | 11/2002 | Wrenn, Jr. | 623/1.42 |
| 6,495,579 B1 | 12/2002 | Hunter | 514/365 |
| 6,506,437 B1 | 1/2003 | Harish et al. | 427/2.25 |
| 6,515,016 B2 | 2/2003 | Hunter | 514/449 |
| 6,569,195 B2 | 5/2003 | Yang et al. | 623/1.46 |
| 6,585,755 B2 | 7/2003 | Jackson et al. | 623/1.15 |
| 6,589,266 B2 | 7/2003 | Whitcher et al. | |
| 6,652,581 B1 | 11/2003 | Ding | 623/1.39 |
| 6,656,217 B1 | 12/2003 | Herzog, Jr. et al. | 623/1.15 |
| 6,689,803 B2 | 2/2004 | Hunter | 514/365 |
| 6,702,849 B1 | 3/2004 | Dutta et al. | 623/1.42 |
| 6,702,850 B1 | 3/2004 | Byun et al. | 623/1.44 |
| 6,730,313 B2 | 5/2004 | Helmus et al. | 424/423 |
| 6,752,829 B2 | 6/2004 | Kocur et al. | 623/1.42 |
| 6,759,431 B2 | 7/2004 | Hunter et al. | 514/449 |
| 6,794,485 B2 | 9/2004 | Shalaby et al. | 528/354 |
| 6,838,493 B2 | 1/2005 | Williams et al. | 523/124 |
| 6,860,946 B2 | 3/2005 | Hossainy et al. | 118/319 |
| 6,932,930 B2 | 8/2005 | DeSimone et al. | 264/235 |
| 6,939,375 B2 | 9/2005 | Sirhan et al. | 623/1.42 |
| 6,939,376 B2 | 9/2005 | Shulze et al. | 623/1.42 |
| 6,979,348 B2 | 12/2005 | Sundar | 623/1.15 |
| 6,989,071 B2 | 1/2006 | Kocur et al. | 156/293 |
| 6,991,804 B2 | 1/2006 | Helmus et al. | 424/423 |
| 7,005,137 B1 | 2/2006 | Hossainy et al. | 424/423 |
| 7,025,777 B2 | 4/2006 | Moore | 623/1.15 |
| 7,037,332 B2 | 5/2006 | Kutryk et al. | 623/1.48 |
| 7,041,127 B2 | 5/2006 | Ledergerber | 623/1.31 |
| 7,041,130 B2 | 5/2006 | Santini, Jr. et al. | 623/1.42 |
| 7,048,939 B2 | 5/2006 | Elkins et al. | 424/423 |
| 7,055,237 B2 | 6/2006 | Thomas | 29/458 |
| 7,056,338 B2 | 6/2006 | Shanley et al. | 623/1.42 |
| 7,056,339 B2 | 6/2006 | Elkins et al. | 623/1.46 |
| 7,070,858 B2 | 7/2006 | Shalaby et al. | 428/411.1 |
| 7,125,837 B1 | 10/2006 | Keating et al. | 514/2 |
| 7,128,755 B2 | 10/2006 | Su et al. | 623/1.15 |
| 7,160,592 B2 | 1/2007 | Rypacek et al. | 428/36.9 |
| 7,163,555 B2 | 1/2007 | Dinh | 623/1.42 |
| 7,166,570 B2 | 1/2007 | Hunter et al. | 514/2 |
| 7,169,404 B2 | 1/2007 | Hossainy et al. | 424/423 |
| 7,311,980 B1 * | 12/2007 | Hossainy et al. | 428/480 |
| 7,875,284 B2 * | 1/2011 | Reyes et al. | 424/423 |
| 7,919,108 B2 * | 4/2011 | Reyes et al. | 424/423 |
| 8,147,540 B2 * | 4/2012 | Reyes et al. | 623/1.46 |
| 2002/0013298 A1 | 1/2002 | Hunter | 514/113 |
| 2002/0051730 A1 | 5/2002 | Bodnar et al. | |
| 2002/0055666 A1 | 5/2002 | Hunter et al. | 600/1 |
| 2002/0082679 A1 | 6/2002 | Sirhan et al. | 623/1.15 |
| 2002/0111603 A1 | 8/2002 | Cheikh | 604/891.1 |
| 2002/0133224 A1 | 9/2002 | Bajgar et al. | 623/1.39 |
| 2003/0004565 A1 | 1/2003 | Harnek et al. | 623/1.15 |
| 2003/0004568 A1 | 1/2003 | Ken et al. | 623/1.46 |
| 2003/0009145 A1 | 1/2003 | Strukjker-Boudier et al. | 604/500 |
| 2003/0077310 A1 | 4/2003 | Pathak et al. | 424/423 |
| 2003/0083732 A1 | 5/2003 | Stinson | 623/1.15 |
| 2003/0083740 A1 | 5/2003 | Pathak | 623/1.43 |
| 2003/0088307 A1 | 5/2003 | Shulze et al. | 623/1.15 |
| 2003/0105588 A1 | 6/2003 | Chen et al. | 424/423 |
| 2003/0139800 A1 | 7/2003 | Campbell | 623/1.15 |
| 2003/0144570 A1 | 7/2003 | Hunter et al. | 600/1 |
| 2003/0153971 A1 | 8/2003 | Chandrasekaran | 623/1.15 |
| 2003/0153972 A1 | 8/2003 | Helmus | 623/1.15 |
| 2003/0157187 A1 | 8/2003 | Hunter | 424/600 |
| 2003/0158598 A1 | 8/2003 | Ashton et al. | 623/1.42 |
| 2003/0190341 A1 | 10/2003 | Shalaby et al. | 424/423 |
| 2003/0190406 A1 | 10/2003 | Hossainy et al. | 427/2.25 |
| 2003/0191449 A1 | 10/2003 | Nash et al. | 604/523 |
| 2003/0195611 A1 | 10/2003 | Greenhalgh et al. | 623/1.15 |
| 2003/0215564 A1 | 11/2003 | Heller et al. | |
| 2003/0216803 A1 | 11/2003 | Ledergerber | 623/1.13 |
| 2003/0225450 A1 | 12/2003 | Shulze et al. | 623/1.15 |
| 2003/0229393 A1 | 12/2003 | Kutryk et al. | 623/1.46 |
| 2003/0231984 A1 | 12/2003 | Bright et al. | 422/57 |
| 2004/0002755 A1 | 1/2004 | Fischell et al. | 623/1.42 |
| 2004/0010306 A1 | 1/2004 | Freyman et al. | 623/1.15 |
| 2004/0024450 A1 | 2/2004 | Shulze et al. | 623/1.42 |
| 2004/0030380 A1 | 2/2004 | Shulze et al. | 623/1.42 |
| 2004/0034337 A1 | 2/2004 | Boulais et al. | 604/890.1 |
| 2004/0039441 A1 | 2/2004 | Rowland et al. | 623/1.42 |
| 2004/0072799 A1 | 4/2004 | Li et al. | 514/58 |
| 2004/0073284 A1 | 4/2004 | Bates et al. | |
| 2004/0098090 A1 | 5/2004 | Williams et al. | 623/1.13 |
| 2004/0098106 A1 | 5/2004 | Williams et al. | 623/1.15 |
| 2004/0098120 A1 | 5/2004 | Williams et al. | 623/1.46 |
| 2004/0106985 A1 | 6/2004 | Jang | 623/1.16 |
| 2004/0106987 A1 | 6/2004 | Palasis et al. | 623/1.42 |
| 2004/0127475 A1 | 7/2004 | New et al. | 514/171 |
| 2004/0133270 A1 | 7/2004 | Grandt | 623/1.42 |
| 2004/0133271 A1 | 7/2004 | Jang | 623/1.42 |
| 2004/0172127 A1 | 9/2004 | Kantor | 623/1.16 |
| 2004/0193257 A1 | 9/2004 | Wu et al. | 623/1.46 |
| 2004/0199241 A1 | 10/2004 | Gravett et al. | 623/1.13 |
| 2004/0199247 A1 | 10/2004 | Kang et al. | 623/1.42 |
| 2004/0215315 A1 | 10/2004 | Jones et al. | 623/1.11 |
| 2004/0215335 A1 | 10/2004 | Brin et al. | 623/1.42 |
| 2004/0220665 A1 | 11/2004 | Hossainy et al. | 623/1.42 |
| 2004/0224023 A1 | 11/2004 | Hunter et al. | 424/486 |
| 2004/0236415 A1 | 11/2004 | Thomas | 623/1.42 |
| 2004/0249441 A1 | 12/2004 | Miller et al. | 623/1.15 |
| 2004/0249443 A1 | 12/2004 | Shanley et al. | 623/1.15 |

(56) References Cited

U.S. PATENT DOCUMENTS

| | | |
|---|---|---|
| 2004/0253203 A1 | 12/2004 | Hossainy et al. .......... 424/78.08 |
| 2004/0254635 A1 | 12/2004 | Shanley et al. .............. 623/1.17 |
| 2004/0254638 A1 | 12/2004 | Byun et al. ................... 623/1.46 |
| 2004/0260318 A1 | 12/2004 | Hunter et al. ................. 606/153 |
| 2004/0260386 A1 | 12/2004 | Shalaby ........................ 623/1.15 |
| 2005/0010170 A1 | 1/2005 | Shanley et al. ............. 604/93.01 |
| 2005/0010275 A1 | 1/2005 | Sahatjian et al. ............ 623/1.11 |
| 2005/0033399 A1 | 2/2005 | Richter ......................... 623/1.11 |
| 2005/0033414 A1 | 2/2005 | Zhang et al. ................. 623/1.15 |
| 2005/0038499 A1 | 2/2005 | Nabel et al. .................. 623/1.15 |
| 2005/0038505 A1 | 2/2005 | Shulze et al. ................. 623/1.42 |
| 2005/0043751 A1 | 2/2005 | Phan et al. .................... 606/155 |
| 2005/0043752 A1 | 2/2005 | Phan et al. .................... 606/155 |
| 2005/0043787 A1 | 2/2005 | Kutryk et al. ................ 623/1.42 |
| 2005/0055078 A1 | 3/2005 | Campbell ..................... 623/1.11 |
| 2005/0060041 A1 | 3/2005 | Phan et al. .................... 623/23.7 |
| 2005/0060042 A1 | 3/2005 | Phan et al. .................... 623/23.7 |
| 2005/0060044 A1 | 3/2005 | Roschak et al. ........... 623/23.65 |
| 2005/0070996 A1 | 3/2005 | Dinh et al. ................... 623/1.42 |
| 2005/0079200 A1 | 4/2005 | Rathenow et al. ............ 424/423 |
| 2005/0096388 A1 | 5/2005 | Hunter et al. ................. 514/509 |
| 2005/0096728 A1 | 5/2005 | Ramer ......................... 623/1.15 |
| 2005/0100577 A1 | 5/2005 | Parker et al. .................. 424/423 |
| 2005/0101635 A1 | 5/2005 | Hunter et al. ................. 514/332 |
| 2005/0107291 A1 | 5/2005 | Hunter et al. ................... 514/11 |
| 2005/0107870 A1 | 5/2005 | Wang et al. .................. 623/1.44 |
| 2005/0112170 A1 | 5/2005 | Hossainy et al. ............. 424/423 |
| 2005/0112172 A1 | 5/2005 | Pacetti ........................... 424/423 |
| 2005/0118344 A1 | 6/2005 | Pacetti ........................... 427/422 |
| 2005/0119720 A1 | 6/2005 | Gale et al. .................... 623/1.11 |
| 2005/0123582 A1 | 6/2005 | Sung et al. .................... 424/426 |
| 2005/0123583 A1 | 6/2005 | Sung et al. .................... 424/426 |
| 2005/0129734 A1 | 6/2005 | Won et al. ..................... 424/423 |
| 2005/0129736 A1 | 6/2005 | Hunter et al. ................. 424/426 |
| 2005/0137148 A1 | 6/2005 | Hunter et al. ................... 514/28 |
| 2005/0137381 A1 | 6/2005 | Pacetti ........................... 528/272 |
| 2005/0137611 A1 | 6/2005 | Escudero et al. ............. 606/108 |
| 2005/0137715 A1 | 6/2005 | Phan et al. .................. 623/23.65 |
| 2005/0171600 A1 | 8/2005 | Harnek et al. ................ 623/1.42 |
| 2005/0187605 A1 | 8/2005 | Greenhalgh et al. ......... 623/1.15 |
| 2005/0187607 A1 | 8/2005 | Akhtar et al. ................. 623/1.15 |
| 2005/0192235 A1 | 9/2005 | Hunter et al. ................... 514/34 |
| 2005/0208091 A1 | 9/2005 | Pacetti ........................... 424/423 |
| 2005/0209680 A1 | 9/2005 | Gale et al. .................... 623/1.15 |
| 2005/0216074 A1 | 9/2005 | Sahatjian et al. ............ 623/1.11 |
| 2005/0228492 A1 | 10/2005 | DeSimone et al. .......... 623/1.49 |
| 2005/0232971 A1 | 10/2005 | Hossainy et al. ............. 424/426 |
| 2005/0233062 A1 | 10/2005 | Hossainy et al. ............. 427/2.1 |
| 2005/0244363 A1 | 11/2005 | Hossainy et al. ........... 424/78.3 |
| 2005/0245637 A1 | 11/2005 | Hossainy et al. ............. 523/113 |
| 2005/0246009 A1 | 11/2005 | Toner et al. ................... 623/1.11 |
| 2005/0249770 A1 | 11/2005 | Hunter .......................... 424/423 |
| 2005/0261760 A1 | 11/2005 | Weber .......................... 623/1.38 |
| 2005/0266038 A1 | 12/2005 | Glauser et al. ................ 424/423 |
| 2006/0008503 A1 | 1/2006 | Shanley et al. ............... 424/425 |
| 2006/0009834 A1 | 1/2006 | Sundar .......................... 623/1.12 |
| 2006/0025713 A1 | 2/2006 | Rosengart et al. ........... 604/5.02 |
| 2006/0034888 A1 | 2/2006 | Pacetti et al. ................. 424/426 |
| 2006/0041102 A1 | 2/2006 | Hossainy et al. ............. 528/354 |
| 2006/0047095 A1 | 3/2006 | Pacetti ........................... 526/242 |
| 2006/0058868 A1 | 3/2006 | Gale et al. .................... 623/1.15 |
| 2006/0067908 A1 | 3/2006 | Ding .......................... 424/78.27 |
| 2006/0095122 A1 | 5/2006 | Pacetti ........................... 623/1.46 |
| 2006/0115449 A1 | 6/2006 | Pacetti ........................ 424/78.27 |
| 2006/0115513 A1 | 6/2006 | Hossainy et al. ............. 424/423 |
| 2006/0121080 A1 | 6/2006 | Lye et al. ....................... 424/423 |
| 2006/0121088 A1 | 6/2006 | Hunter et al. ................. 424/426 |
| 2006/0134165 A1 | 6/2006 | Pacetti ........................... 424/422 |
| 2006/0142541 A1 | 6/2006 | Hossainy ...................... 528/354 |
| 2006/0147412 A1 | 7/2006 | Hossainy et al. .......... 424/78.27 |
| 2006/0160985 A1 | 7/2006 | Pacetti et al. ................. 528/272 |
| 2006/0246108 A1 | 11/2006 | Pacetti et al. ................. 424/426 |
| 2006/0246109 A1 | 11/2006 | Hossainy et al. ............. 424/426 |
| 2006/0269586 A1 | 11/2006 | Pacetti ........................... 424/423 |
| 2006/0280770 A1 | 12/2006 | Hossainy et al. ............. 424/423 |
| 2007/0005130 A1 | 1/2007 | Glauser et al. ................ 623/1.38 |
| 2007/0196423 A1* | 8/2007 | Ruane et al. ................... 424/423 |
| 2007/0212394 A1 | 9/2007 | Reyes et al. | |
| 2008/0020013 A1 | 1/2008 | Reyes et al. | |
| 2010/0197944 A1 | 8/2010 | Palle et al. | |

FOREIGN PATENT DOCUMENTS

| | | | |
|---|---|---|---|
| WO | WO 93/23555 A1 | 11/1993 | .............. C12P 17/02 |
| WO | WO 93/24476 A1 | 12/1993 | ........... C07D 305/14 |
| WO | WO 94/00156 A1 | 1/1994 | .............. A61K 47/48 |
| WO | WO 94/07876 A1 | 4/1994 | ........... C07D 305/14 |
| WO | WO 94/07880 A1 | 4/1994 | ........... C07D 305/14 |
| WO | WO 94/07881 A1 | 4/1994 | ........... C07D 305/14 |
| WO | WO 94/07882 A1 | 4/1994 | ........... C07D 305/14 |
| WO | WO 94/20089 A1 | 9/1994 | ........... A61K 31/335 |
| WO | WO 95/19796 A1 | 7/1995 | .............. A61L 27/00 |
| WO | WO 96/37165 A1 | 11/1996 | ................ A61F 2/00 |
| WO | WO 00/45744 | 8/2000 | ................ A61F 2/06 |
| WO | WO 03/006180 A1 | 1/2003 | ................ B05D 1/04 |
| WO | WO 2004/028582 A1 | 4/2004 | |
| WO | WO 2005/004946 A1 | 1/2005 | .............. A61L 31/18 |
| WO | WO 2005/089855 A1 | 9/2005 | |

OTHER PUBLICATIONS

Eckhard Alt, MD, Iris Haehnel, MD, Christine Beilharz, MD, Klaus Prietzel, MD, Daniel Preter, MD, Axel Stemberger, PhD, Thilo Fliedner, MD, Wolf Erhardt, MD, Albert Schömig, MD; *Inhibition of Neointima Formation After Experimental Coronary Artery Stenting a New Biodegradable Stent Coating Releasing Hirudin and the Prostacyclin Analogue Iloprost*; 2000; American Heart Association, Inc www.circulationaha.org.

Duane E. Cutright, Colonel, DC, USA, Bienvenido Perez, Lieutenant Colonel, DC, USA, Joe D. Beasley, III, Major, DC, USA, Wayne J. Larson, Lieutenant Colonel, DC, USA, and William R. Posey, Lieutenant Colonel, DC, USA; *Degradation rates of polymers and copolymers of polylactic and polyglycolic acids*; Jan. 1974; Oral Surgery United States Army Institute of Dental Research, Walter Reed Army Medical Center, Washington DC.

B.M.P. Ferreira, C.A.C. Zavaglia, E.A.R. Duek; *Films of Poly (L-Lactic Acid)/Poly (Hydroxybutyrate-co-Hydroxyvalerate) Blends: In vitro Degradation*; Jan. 18, 2001; Materials Research ISSN 1516-1439.

E.J. Frazza and E.E. Schmitt; *A New Absorbable Suture*; 1971; J. Biomed. Mater. Res. Symposium vol. 1, pp. 43-58.

Caroline A. Kavanagh, Yuri A. Rochev, William M. Gallagher, Kenneth A. Dawson, Alan K. Keenan; *Local drug delivery in restenosis injury; thermoresponsive co-polymers as potential drug delivery systems*; Jan. 2004; Pharmacology & Therapeutics 102 pp. 1-15.

Menemşe Kiremitçi-Gümüşderelioğlu and Günday Deniz; *Synthesis, Characterization and in Vitro Degradation of Poly(DL-Lactide)/Poly(DL-Lactide-co-Glycolide) Films*; May 5, 1998; Turk J Chem 23 (1999), pp. 153-161.

A. Michael Lincoff, MD, FACC, Joseph G. Furst, MS. Stephen G. Ellis, MD, FACC, Ronald J. Tuch, MS, Eric J. Topol, MD, FACC; *Sustained Local Delivery of Dexamethasone by a Novel Intravascular Eluting Stent to Prevent Restenosis in the Porcine Coronary Injury Model*; Mar. 15, 1997; JACC vol. 29, No. 4 pp. 808-816.

Hideo Tamai, MD, Keiji Igaki, Eisho Kyo, MD, Kunihiko Kosuga, MD, Akiyoshi Kawashima, MD, Shigeo Matsui, MD, Hidenori Komori, MD, Takafumi Tsuji, MD, Seiichiro Motohara, MD, Hiromu Uehata, MD; *Initial and 6-Month Results of Biodegradable Poly-l-Lactic Acid Coronary Stents in Humans*; Sep. 28, 1999;Circulation Jul. 25, 2000 pp. 399-404.

Felix Vogt, Andreas Stein, Gösta Rettemeier, Nicole Krott, Rainer Hoffmann, Jürgen vom Dahl, Anja-Katrin Bosserhoff, Walter Michaeli, Peter Hanrath, Christian Weber, Rüdiger Blindt; *Long-term assessment of a novel biodegradable paclitaxel-eluting coronary polylactide sten*; Jan. 14, 2004; European Heart Journal (2004) 25, pp. 1330-1340.

(56) References Cited

OTHER PUBLICATIONS

Yadong Wang, Guillermo A. Ameer, Barbara J. Sheppard, Robert Langer; *A tough biodegradable elastomer*; 2002; Nature Biotechnology 0602-0606.

BS EN ISO 1138-2:2009 corresponding to ISO 11138-2:2006.

Notice of Opposition against European Patent No. 20 043704B1, 5-21012.

Kaopana R. Kamath, James J. Berry, Kathleen M. Miller; *The Taxus™ drug-eluting stent: A new paradigm in controlled drug delivery*; Advanced Drug Delivery Reviews 58 (2006) 412-436.

International Search Report and Written Opinion; PCT/US2009/004810, Aug. 26, 2010.

Han Ya-Ling; Wang, Shou-Li; Jin, Quan-Min; Liu, Hai-Wei; Ma, Ying-Yan; Wang, Zhu-Lu; Wang, Dong-Mei; Luan, Bo and Wang, Geng; "Efficacy of stenting for unprotected left main coronary artery disease in 297 patients," *Chin Med J*, 2006; 119 (7): 544-550.

Han, Ya-Ling; Wang, Shou-Li; Jing, Quan-Min; Li, Yi; Zhang, Jian; Ma, Ying-Yan and Luan, Bo; "Percutaneous coronary intervention for chronic total occlusion in 1263 patients: a single-center report," *Chinese Medical Journal*, 2006; 119 (14): 1165-1170.

Phillip Hanefeld, Ullrich Westedt, Ralf Wombacher, Thomas Kissel, Andreas Schaper, Joachim H. Wendorff, and Andreas Greiner, "Coating of Poly(p-xylylene) by PLA-PEO-PLA Triblock Copolymers with Excellent Polymer-Polymer Adhesion for Stent Applications," *Biomacromolecules* 2006, 7, 2086-2090.

Hidehiko Honda, MD, Taiichiro Meguro, MD, Kaname Takizawa, ME, Shogen Isoyama, MD, "Use of Everolimus-eluting Stent with a Bioresorbable Polymer Coating for Treatment of Recurrent In-stent Restenosis," *The Journal of Invasive Cardiology*, vol. 17, No. 2, 2005 112-115.

Christine Jerome, Abdelhafid Aqil, Samuel Voccia, David-Emmanuel Labaye, Veronique Maquet, Sandrine Gautier, Oliver F. Bertrant, Robert Jerome, "Surface modification of metallic cardiovascular stents by strongly adhering aliphatic polyester coatings," *Wiley Periodicals, Inc.*, 2005 521-529.

Antoine Lafont, Suming Li, Henri Garreau, Frederic Cornhill, Michel Vert, "PLA Stereocopolymers as Sources of Bioresorbable Stents: Preliminary Investigation in Rabbit," *Wiley Periodicals, inc.*, 2006 349-356.

Teemu Lamsa, Haitao Jin, Joonas Mikkonen, Johanna Laukkarinen, Juhani Sand, Isto Nordback, "Biocompatibility of a New Bioabsorbable Radiopaque Stent Material ($BaSO_4$ Containing Poly-L, D-Lactide) in the Rat Pancreas," *Pancreatology*, 2006:6 301-305.

Iikka Uurto, MD, Joonas Mikkonen, MSc, Jyrki Parkkinen, MD, Leo Keski-Nisula, MD, Timo Nevalainen, DVM, Minna Kellomaki, MSc, Pertti Tormala, MSc, and Juha-Pekka Salenius, MD, "Drug-Eluting Biodegradable Poly-D/L-Lactic Acid Vascular Stents: An Experimental Pilot Study," *J Endovasc Ther*, 2005:12 371-379.

* cited by examiner

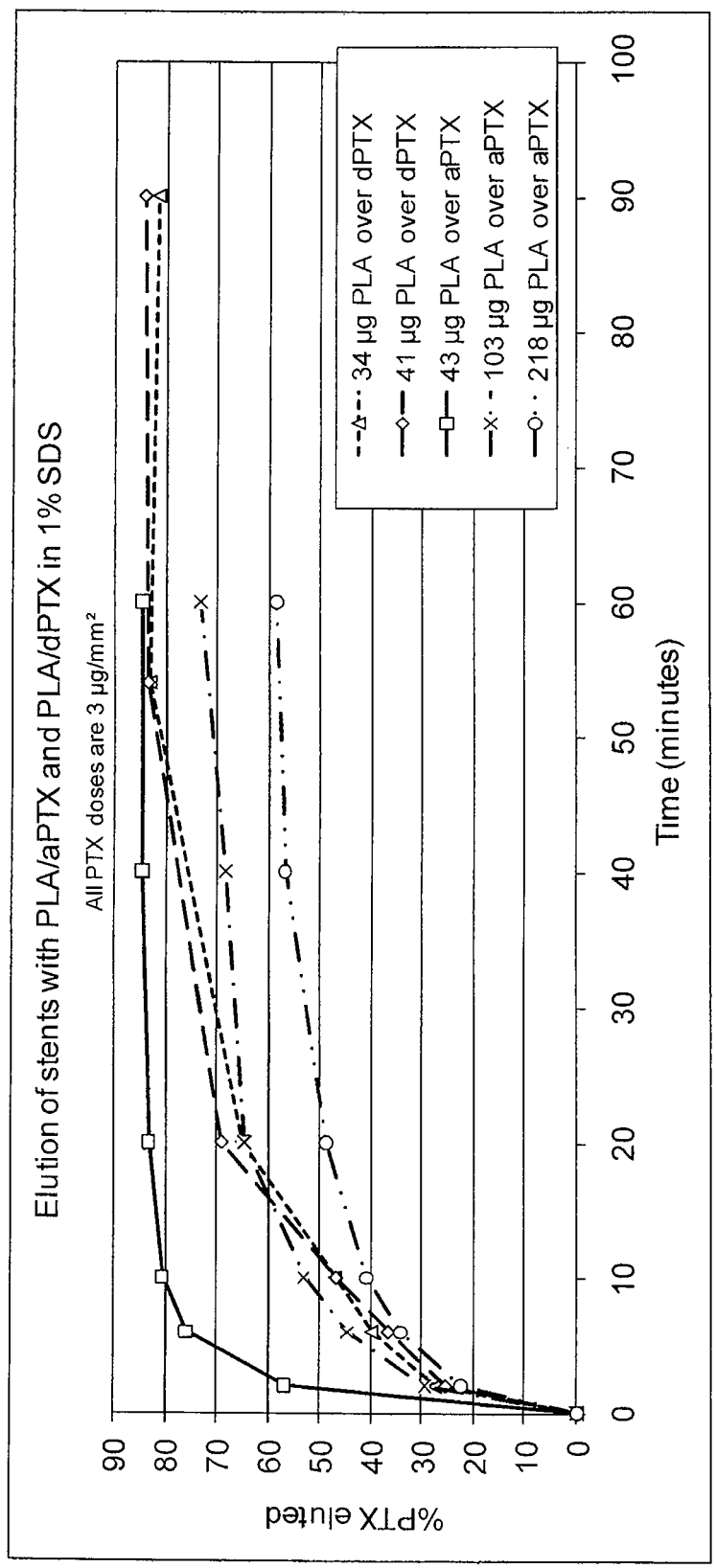

IMPLANTABLE MEDICAL DEVICE COATINGS WITH BIODEGRADABLE ELASTOMER AND RELEASABLE TAXANE AGENT

RELATED APPLICATIONS

This application claims the benefit of the filing date under 35 U.S.C. §119(e) of Provisional U.S. Patent Application Ser. No. 61/091,045, filed Aug. 22, 2008, the contents of which are hereby incorporated by reference.

TECHNICAL FIELD

The present invention relates to implantable medical device coatings configured to release a therapeutic agent, such as a taxane agent. More specifically, the present invention relates to implantable medical device coatings comprising a biodegradable elastomer and a taxane agent, as well as related methods of coating the implantable medical device, and methods for the local administration of the therapeutic agents to a target site in a body vessel.

BACKGROUND

Delivery of a therapeutic agent from an implantable medical device can be desirable for a variety of applications. Therapeutic agents can be released from a medical device, such as an expandable stent or valve, to treat or mitigate undesirable conditions including restenosis, tumor formation or thrombosis. Procedures for mitigating certain conditions can include implantation of a device comprising a therapeutic agent. For example, the implantation of stents during angioplasty procedures has substantially advanced the treatment of occluded body vessels. Angioplasty procedures such as Percutaneous Transluminal Coronary Angioplasty (PCTA) can widen a narrowing or occlusion of a blood vessel by dilation with a balloon. Occasionally, angioplasty may be followed by an abrupt closure of the vessel or by a more gradual closure of the vessel, commonly known as restenosis. Acute closure may result from an elastic rebound of the vessel wall and/or by the deposition of blood platelets and fibrin along a damaged length of the newly opened blood vessel. In addition, restenosis may result from the natural healing reaction to the injury to the vessel wall (known as intimal hyperplasia), which can involve the migration and proliferation of medial smooth muscle cells that continues until the vessel is again occluded. To prevent such vessel occlusion, stents have been implanted within a body vessel. However, restenosis may still occur over the length of the stent and/or past the ends of the stent where the inward forces of the stenosis are unopposed. To reduce this problem, one or more therapeutic agents may be administered to the patient. For example, a therapeutic agent may be administered systemically, locally administered through a catheter positioned within the body vessel near the stent, or coated on the stent itself.

A medical device can be coated with a therapeutic agent in a manner suitable to expose tissue near the implantation site of the medical device to the therapeutic agent over a desired time interval, such as by releasing the therapeutic agent from an implanted stent into surrounding tissue inside a body vessel. Various approaches can be used to control the rate and dose of release of therapeutic agents from an implantable medical device. The design configuration of an implantable device can be adapted to influence the release of therapeutic from the device. A therapeutic agent can be included in the implantable medical device in various configurations. In some devices, the therapeutic agent is contained within an implantable frame or within a coating on the surface of the implantable frame. An implantable frame coating can include a bioabsorbable material mixed with a therapeutic agent, or coated over the therapeutic agent. Some implantable medical devices comprise an implantable frame with a bioabsorbable material mixed with or coated over a therapeutic agent. For example, U.S. Pat. No. 5,624,411 to Tuch, filed Jun. 7, 1995, describes radially expandable stents coated with a porous polymer overlaying a first coating layer containing various bioactive agents. The porous polymer may be a biodegradable polymer, such as poly(lactic acid). Implantable medical devices can also comprise a porous biostable material containing a dissolvable material and a therapeutic agent, where dissolution of the removeable material upon implantation forms pores that release the therapeutic agent. For example U.S. Pat. No. 5,447,724 to Helmus, filed Nov. 15, 1993, describes a two-layer coating comprising an outer layer containing a mixture of a biostable polymer and an elutable component positioned over a bioactive reservoir layer such that the elutable component dissolves away upon implantation of the coating in a body, transforming the outer layer into a porous layer permitting diffusion of the bioactive agent from the reservoir layer through the outer layer and into the body.

The design of a controlled release medical device can also depend on the desired mode of implantation of the device. The device can be adapted to the appropriate biological environment in which it is used. For example, a device for percutaneous transcatheter implantation can be sized and configured for implantation from the distal portion of a catheter, adapted for expansion at the point of treatment within the body vessel by balloon or self-expansion. An implantable medical device can also be adapted to withstand a desired amount of flexion or impact, and should provide delivery of a therapeutic agent with a desired elution rate for a desired period of time.

There is a need for a medical device capable of releasing a therapeutic agent at a desired rate and over a desired time period upon implantation. Preferably, implantation of a medical device releases a therapeutic agent as needed at the site of medical intervention to promote a therapeutically desirable outcome, such as mitigation of restenosis. There is also a need for such a medical device with a releasable therapeutic agent capable of withstanding the flexion and impact that accompany the transportation and implantation of the device without releasing an undesirable amount of the therapeutic agent prior to implantation at a point of treatment. For example, a medical device can include a coating of a bioabsorbable material with sufficient durability to resist the undesirable premature release of the therapeutic agent from the device prior to implantation at a point of treatment within a body vessel.

Paclitaxel, and taxane analogues and derivatives thereof, can be used as a therapeutic agent coated on and released from implantable devices, such as stents, to mitigate or prevent restenosis. Paclitaxel is believed to disrupt mitosis (M-phase) by binding to tubulin to form abnormal mitotic spindles (i.e., a microtubule stabilizing agent).

SUMMARY

The present invention relates to implantable medical device coatings configured to release a taxane agent and to method of using such devices. The implantable medical device preferably includes a multi-layer coating that releases a taxane agent upon implantation in a body vessel. The coating preferably includes at least two layers, with a layer of a bioabsorbable elastomer positioned over a layer comprising the taxane agent. In one embodiment, at least a portion of the taxane agent is a dihydrate solid form of paclitaxel.

One aspect provides a method of delivering a therapeutic agent to a peripheral blood vessel. The method includes the use of a radially-expandable vascular stent having an abluminal side and a luminal side defining a substantially cylindrical lumen and being movable from a radially expanded configuration to a radially compressed configuration. The stent also includes a multi-layer coating on the abluminal surface. The coating includes a first layer including a taxane agent including a first taxane solid form characterized by a vibrational spectrum comprising at least three peaks between 1735 and 1700 $cm^{-1}$, and a second layer positioned over the first layer and including between about 0.05 and 20 mg of a biodegradable elastomer per $mm^2$ of the surface. The biodegradable elastomer has a molecular weight of 75,000-240,000 kDa, and is present in an amount between 1 and 20 times the weight of the taxane agent in the first layer.

The coated vascular stent is intralumenally inserted into the blood vascular system using a means for intralumenal delivery comprising a catheter. The stent is positioned within a peripheral artery; and is radially expanded within the artery so as to place the stent in contact with a portion of a wall of the artery in a manner effective to deliver the taxane agent to the wall of the peripheral artery.

In various embodiments, the biodegradable elastomer includes a polymer or copolymer comprising at least one of: poly(lactic acid), poly(glycolic acid), poly(4-hydroxybutyrate) and poly(glycerol-sibacate). In other embodiments, the biodegradable elastomer is a poly(lactic acid) selected from poly(L-lactic acid), poly(D-lactic acid) and poly(D,L-lactic acid).

In one embodiment, the stent is placed within the iliac artery or the femoral artery.

In another embodiment, the first taxane solid form is dihydrate paclitaxel. In yet another embodiment, dihydrate paclitaxel makes up at least 20% of the taxane agent. In another embodiment dihydrate paclitaxel makes up at least 40% of the taxane agent. In yet another embodiment dihydrate paclitaxel makes up at least 60% of the taxane agent.

Another aspect provides a method for coating an implantable medical device to form a drug delivery system. The method includes depositing a first layer including a taxane agent on the surface of the medical device. The first layer is deposited by applying a first solution including a first solvent and the taxane agent dispersed in the first solvent to the surface. The first solution does not contain a polymer. The first solvent is evaporated and the application and evaporation repeated until the first layer contains between about 0.05 and 1.00 μg of the taxane agent per $mm^2$ of the surface. At least a portion of the taxane agent is present in a first taxane solid form characterized by a vibrational spectrum comprising at least three peaks between 1735 and 1700 $cm^{-1}$.

A second layer comprising a biodegradable elastomer is deposited over the first layer by applying a second solution including a second solvent and a biodegradable elastomer dispersed in the second solvent, the biodegradable elastomer having a molecular weight of 75,000-240,000 kDa. The second solvent is evaporated and the application and evaporation repeated until the weight of the biodegradable elastomer in the second layer is between 1 and 20 times greater than the weight of the taxane agent in the first layer.

In one embodiment, the second solvent is acetone. In another embodiment, at least a portion of the taxane agent is present in a second taxane solid form characterized by a vibrational spectrum having fewer than three peaks between 1735 and 1700 $cm^{-1}$.

Another aspect provides a coated implantable medical device comprising a coating configured to release a taxane agent adhered to a surface of the medical device. The coating includes a first layer including a taxane agent including a first taxane solid form characterized by a vibrational spectrum comprising at least three peaks between 1735 and 1700 $cm^{-1}$, and a second layer positioned over the first layer and including a biodegradable elastomer. The biodegradable elastomer has a molecular weight of 75,000-240,000 kDa, and is present in an amount between 1 and 20 times the weight of the therapeutic agent in the first layer.

In one embodiment, biodegradable elastomer is poly(lactic acid). In another embodiment, the first taxane solid form is dihydrate paclitaxel. In yet another embodiment, the taxane agent comprises at least 40% dihydrate paclitaxel. In another embodiment, the taxane agent comprises at least 60% dihydrate paclitaxel.

BRIEF DESCRIPTION OF THE DRAWINGS

FIG. 5 shows paclitaxel elution profiles in SDS.

DETAILED DESCRIPTION

Figure 1A:
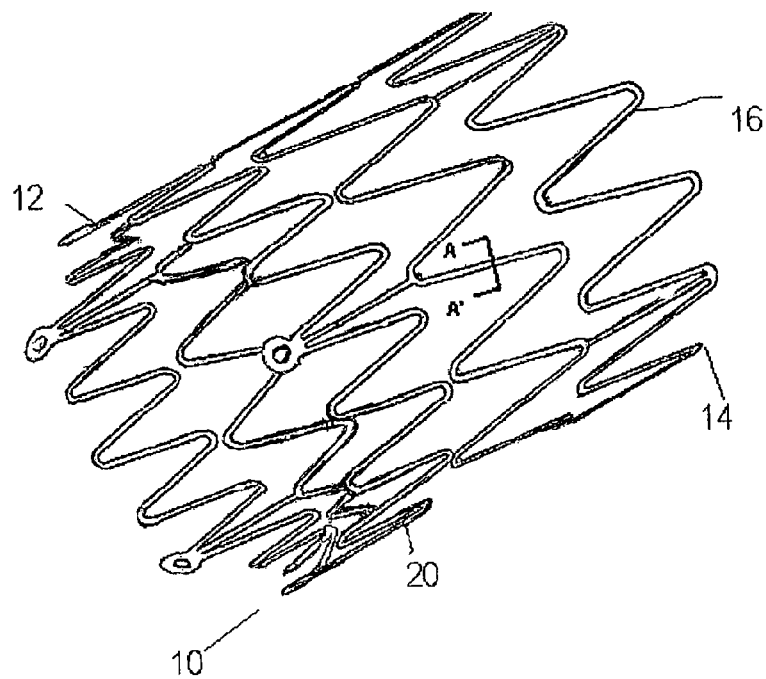
FIG. 1A shows side view of an implantable medical device configured as a coated vascular stent.

The following detailed description and appended drawings describe and illustrate various exemplary embodiments of the invention. The description and drawings serve to enable one skilled in the art to make and use the invention. Discussion of the illustrated coating configurations of certain preferred coated medical device systems comprising a two-layer coating on a vascular stent also relate to other coated medical devices comprising different implantable medical devices (including catheters, stent grafts, vascular grafts, and others) coated with more than two layers, different hydrophobic therapeutic agents, different biodegradable elastomers and/or different layer compositions are also.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The term "hydrophobic," as used herein, refers to a substance with a solubility in water of less than 0.1 mg/mL at room temperature (about 25° C.).

A therapeutic agent is "enclosed" if the therapeutic agent is surrounded by the coating or other portions of the medical device, and does not form a portion of the surface area of the medical device prior to release of the therapeutic agent. When a medical device is initially placed in an elution medium, an enclosed therapeutic agent is preferably not initially in contact with the elution medium.

The term "elution," as used herein, refers to removal of a material from a medical device coating upon contact with an elution medium. The elution medium can remove the material from the substrate by any process, including by acting as a solvent with respect to the removable material. For example, in medical devices adapted for introduction to the vascular system, blood can act as an elution medium that dissolves a therapeutic agent releasably associated with a portion of the surface of the medical device. The removable material preferably includes the therapeutic agent, but can also include a bioabsorbable elastomer. The elution profile of a given coating configuration and composition typically varies in different elution media.

An "elution medium," as used herein, refers to a condition or environment into which a therapeutic agent can be released from a coating upon contact of the coating with the elution medium. The elution medium is desirably a fluid. More desirably, the elution medium is a biological fluid such as blood or porcine serum, although any other chemical substance can be used as an elution medium. For example, alternative elution media include phosphate buffered saline, aqueous solutions, reaction conditions including temperature and/or pH, or combinations thereof, that release the therapeutic agent at a desired rate. Preferably, the elution medium is a fluid that provides an elution profile that is similar to the elution profile obtained upon implantation of the medical device within a body vessel. For example, porcine serum can provide an elution profile that is similar to the elution profile in blood for some coating configurations.

The term "effective amount" refers to an amount of an active ingredient sufficient to achieve a desired affect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the composition of the present invention.

The terms "about" or "substantially" used with reference to a quantity includes variations in the recited quantity that are equivalent to the quantity recited, such as an amount that is insubstantially different from a recited quantity for an intended purpose or function.

The term "luminal surface," as used herein, refers to the portion of the surface area of a medical device defining at least a portion of an interior lumen. Conversely, the term "abluminal surface," as used herein, refers to portions of the surface area of a medical device that do not define at least a portion of an interior lumen. For example, where the medical device is a tubular frame formed from a plurality of interconnected struts and bends defining a cylindrical lumen, the abluminal surface includes the exterior surface, sides and edges of the struts and bends, while the luminal surface can include the interior surface of the struts and bends.

The term "interface," as used herein, refers to a common boundary between two structural elements, such as two coating layers in contact with each other.

The term "coating," as used herein and unless otherwise indicated, refers to material attached to an implantable medical device. A coating can include material covering any portion of a medical device, and can be configured with one or more coating layers. A coating can have a substantially constant or a varied thickness and composition. Coatings can be adhered to any portion of a medical device surface, including the luminal surface, the abluminal surface, or any portions or combinations thereof.

The term "coating layer," as used herein, refers to a material positioned over a substrate surface. A coating layer material can be positioned in contact with the substrate surface, or in contact with other material(s) between the substrate surface and the coating layer material. A coating layer can cover any portion of the surface of a substrate, including material positioned in separate discrete portions of the substrate or a continuous layer over an entire substrate surface.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "alloy" refers to a substance composed of two or more metals or of a metal and a nonmetal intimately united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The term "bioabsorbable" refers to materials selected to dissipate upon implantation within a body, independent of which mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

The terms "absorption," "bioresorption" and "bioabsorption" can be used interchangeably to refer to the ability of the polymer or its degradation products to be removed by biological events, such as by fluid transport away from the site of implantation or by cellular activity (e.g., phagocytosis). The term "bioabsorbable" will generally be used in the following description to encompass resorbable, absorbable, bioresorbable, and biodegradable.

A "biocompatible" material is a material that is compatible with living tissue or a living system by not being toxic or injurious.

A "non-bioabsorbable" or "biostable" material refers to a material, such as a polymer or copolymer, which remains in the body without substantial bioabsorption.

The phrase "controlled release" refers to an alteration of the rate of release of a therapeutic agent from a medical device coating in a given environment. A coating or configuration that alters the rate at which the therapeutic agent is released from a medical device provides for the controlled release of the therapeutic agent. A "sustained release" refers to prolonging the rate or duration of release of a therapeutic agent from a medical device. The rate of a controlled release of a therapeutic agent may be constant or vary with time. A controlled release may be characterized by a drug elution profile, which shows the measured rate at which the therapeutic agent is released from a drug-coated device in a given elution medium as a function of time. A controlled release elution profile may include, for example, an initial burst release associated with the introduction of the medical device into the physiological environment, followed by a more gradual subsequent release.

An "anti-proliferative" agent/factor/drug indicates any protein, peptide, chemical or molecule that acts to inhibit cell division. Examples of anti-proliferative agents include microtubule inhibitors such as vinblastine, vincristine, colchicine and paclitaxel, or other agents such as cisplatin.

The term "pharmaceutically acceptable," as used herein, refers to those compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic salt forms of the compounds of the invention.

When naming substances that can exist in multiple enantiomeric forms, reference to the name of the substance without an enantiomeric designation, such as (d) or (l), refers herein to the genus of substances including the (d) form, the (l) form and the racemic mixture (e.g., d,l), unless otherwise specified. For example, recitation of "poly(lactic acid)," unless otherwise indicated, refers to a compound selected from the group consisting of: poly(L-lactic acid), poly(D-lactic acid) and poly(D,L-lactic acid). Similarly, generic reference to compounds that can exist in two or more polymorphs is understood to refer to the genus consisting of each individual polymorph species and any combinations or mixtures thereof.

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to one polymer or a mixture comprising two or more polymers.

Coating Configurations

A first embodiment provides an implantable medical device including a multi-layer coating that releases a therapeutic agent, such as a taxane agent, upon implantation in a body vessel. In one embodiment, the coating includes at least two layers: a first layer comprising a therapeutic agent positioned between at least a portion of the surface of the medical device and a second layer comprising a bioabsorbable elastomer positioned over and covering at least a portion of the first layer.

In one embodiment, the medical device is preferably configured to position the second layer between the first layer and the wall of a body vessel upon implantation. In another embodiment, the medical device structure defines an interior lumen with a luminal (interior) surface positioned radially opposite an abluminal (exterior) surface. The coating can be applied to the luminal and/or the abluminal surface. In one embodiment, a therapeutic agent is releasably attached to the abluminal surface. Optionally, a second therapeutic agent can be releasably attached to the luminal surface. One or more bioabsorbable elastomers can cover the therapeutic agent(s). The bioabsorbable elastomer preferably encloses the therapeutic agent(s), and can be applied to the abluminal surface as well as the luminal surface of the medical device. Each coating layer can be applied to a portion of a surface or can be applied continuously over the entire surface, depending on the device configuration desired.

FIG. 1 shows an exemplary coated medical device configured as a coated implantable vascular stent 10 having a two layer coating over a radially expandable frame 20. The vascular stent 10 can be a tubular stent formed from a plurality of connected hoops 12 formed from a sinusoidal array of alternating struts and bends. The vascular stent 10 can be radially expandable from compressed state to the expanded state shown in FIG. 1. The frame 20 can be formed from any suitable material, such as a superelastic nickel-titanium alloy.

The abluminal surface 14 of the frame 20 can be coated with a first layer 30 comprising the therapeutic agent, and a second layer 40 positioned over at least the first layer 30. The second layer 40 comprises a bioabsorbable elastomer. In one embodiment, the first layer 30 consists essentially of a therapeutic agent releasably adhered to at least a portion of the abluminal surface 14 of an implantable medical device frame 20, and positioned between the abluminal surface 14 of the implantable medical device 20 and a second layer 40 consisting essentially of a bioabsorbable elastomer material. In one embodiment, the first layer 30 contains a therapeutically effective amount of the therapeutic agent. In another embodiment, the first layer 30 is substantially free of a polymer, such as the biodegradable elastomer present in the second layer 40. The second layer 40 can be positioned over at least the first layer 30 and is optionally positioned over all or part of the abluminal surface of the medical device. In one embodiment, the second layer 40 can be substantially free of the therapeutic agent. For example, the second layer 40 may consist essentially of a biodegradable elastomer containing less than about 0.1 mg of the therapeutic agent per $mm^2$ surface area of the second layer 40.

Figure 1B:
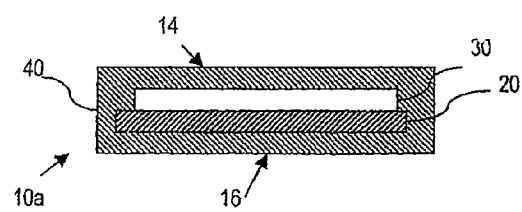
FIG. 1B shows a cross sectional view of a portion of the coated vascular stent of FIG. 1A.
Figure 1C:
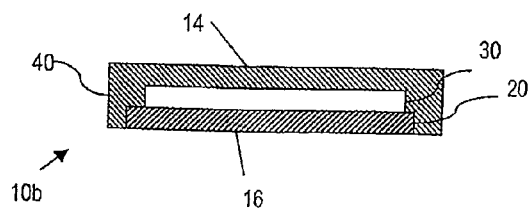
FIG. 1C shows a cross sectional view of a portion of a first alternative coating configuration for the coated vascular stent of FIG. 1A.

The first layer 30 and the second layer 40 can have any suitable thickness. FIG. 1B shows a cross section of a coated portion of the frame 20 along the line A-A' in FIG. 1A, including the luminal surface 14 and the abluminal surface 16. In the embodiment illustrated in FIG. 1B, the first layer 30 can consist essentially of a therapeutic agent adhered directly to the abluminal surface of the frame 20, and the second layer 40 positioned over both the first layer 30 and the luminal surface 16 of the frame 20. Alternatively, as shown in the cross sectional view of the frame 20 along the line A-A' of FIG. 1C, the second layer 40 can be deposited over only the luminal surface 14 of the frame 20, without being deposited over the abluminal surface 16 of the frame 20. In one embodiment, the second layer 40 encloses the first layer 30, such that the exterior surface of the coating does not include the uncovered therapeutic agent prior to elution of the therapeutic agent.

The coating can be applied to any suitable surface of a medical device, including on substantially flat or roughened metal surfaces, impregnation within tissue grafts or polymer gels, within grooves, holes or wells formed in portions of a device. In one embodiment, the medical device is configured as a vascular stent or stent graft, although the coatings can be applied to any suitable implantable medical device. For example, implantable portions of catheters, biliary or urological stents or shunts, stent grafts, tissue grafts, orthopedic implants, pacemakers, implantable valves and other implantable devices can be coated with the coatings disclosed herein, so as to release a therapeutic agent upon implantation.

Figure 2A:
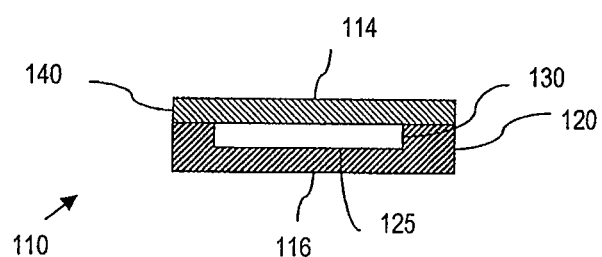
FIG. 2A shows a cross sectional view of a portion of a second alternative device configuration for the coated vascular stent of FIG. 1A.

In other embodiments, the invention may include a layer(s) in which the therapeutic agent is contained within the medical device itself. The medical device may have holes, wells, slots, grooves, or the like for containing the therapeutic agent and/or polymer (see, e.g., co-pending U.S. application Ser. No. 10/870,079, incorporated herein by reference). FIG. 2A shows a cross section of a coated portion of a medical device 110, such as a modified version of the medical device of FIG. 1A along the line A-A'. The medical device includes a frame 120 that has a well 125 that contains the first layer 130 comprising a therapeutic agent. The first layer 130 is similar to the first layer 30 described above, except that it is positioned within the well 125 instead of above the surface of the medical device 110. The first layer 130 is enclosed by the walls of the well 125 and the second layer 140. The well 125 can have any suitable dimensions, and can be formed in the medical device by any suitable method, including the mechanical or chemical removal of portions of the medical device frame. A second layer 140 comprising a bioabsorbable elastomer is positioned over the first layer 130 and on the abluminal surface 114 of the medical device 110. The second layer 140 is similar to the second layer 40 described above. The luminal surface 116 of the medical device 110 can be uncoated. Alternatively, the therapeutic agent and/or bioabsorbable elastomer may be incorporated into a biodegradable medical device frame 120 that releases the therapeutic agent as the device degrades, or the therapeutic agent and/or bioabsorbable elastomer may be incorporated into or placed on the medical device frame 120 in any other known manner.

Figure 2B:
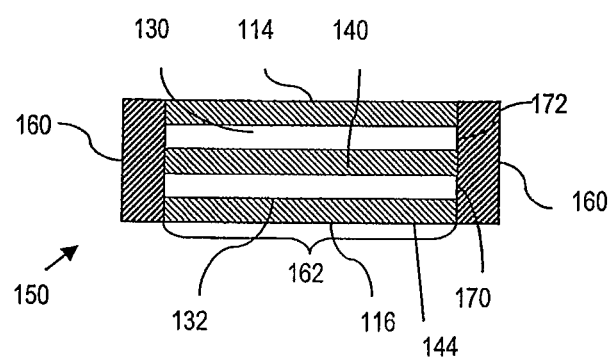
FIG. 2B shows a cross sectional view of a portion of a third alternative coating configuration for the coated vascular stent of FIG. 1A.

Optionally, the medical device coating can further include more than two layers. FIG. 2B shows a cross section of a coated portion of a medical device 150, such as a modified version of the medical device of FIG. 1A along the line A-A'. The medical device includes a frame 160 that has a hole 162 extending between the luminal surface 116 and the abluminal surface 114 that contains a plurality of layers 170 within the hole 162. The layers 170 include a first therapeutic layer 130 and a second therapeutic layer 132 that comprise the same of different therapeutic agent(s). For example, a first coating layer 140 can be positioned between the first therapeutic layer 130 and the second therapeutic layer 132, a second coating layer 142 can be positioned on the abluminal side of the first therapeutic layer 130 and a third coating layer 144 can be positioned on the luminal side of the second therapeutic layer 132. The first coating layer 140, the second coating layer 142 and the third coating layer 144 can have compositions and thicknesses that are the same or different. Preferably, the first coating layer 140 and the second coating layer 142 include a bioabsorbable elastomer. The third coating layer 144 can include a material that functions to direct the elution of the therapeutic agent toward the abluminal surface 114 of the medical device, or to slow the elution rate of the therapeutic agent elution on the luminal side. The second coating layer 142 can be formed from a bioabsorbable material that is more porous than or degrades more rapidly than the first coating layer 140 upon implantation. Accordingly, the first therapeutic layer 130 can elute from the abluminal surface 114 before or more rapidly than the second therapeutic layer 132. The rapid elution of the first therapeutic layer 130 can provide an initial "burst" of the therapeutic agent to a portion of the body vessel contacting the abluminal surface 114, followed by a more gradual and sustained elution from the second therapeutic layer 132 to the abluminal surface 114.

The plurality of layers 170 in the coating can include any suitable numbers of layers comprising the therapeutic agent and layers comprising other coating materials such as bioabsorbable elastomers, including 2, 3, 4, 5, 6, 7, 8, 9, or 10-layer coatings. Preferably, layers comprising a bioabsorbable elastomer are positioned between layers comprising one or more therapeutic agent(s). Different therapeutic agents can be placed in different layers or within the same layer. Alternatively, a layer such as the third coating layer 144 can be formed from a bioabsorbable material to permit elution of the therapeutic agent toward the luminal surface 116. In yet another alternative coating configuration, the first coating layer 140 can be formed from a biostable material and the second coating layer 142 and the third coating layer 144 can be formed from a bioabsorbable elastomer permitting elution of the first therapeutic layer 130 from the abluminal surface 114 and the second therapeutic layer 132 from the luminal surface 116.

In other embodiments, additional layers other than layers containing the therapeutic agent or the bioabsorbable elastomer can be placed between the first layer comprising the therapeutic agent and the surface of the medical device, between the first layer and the second layer or over the second layer. The optional additional layers can, for example, promote adhesion of the therapeutic agent to the medical device or to desirably affect the release of the therapeutic agent. For example, an adhesion promoting layer can be deposited between the frame 160 in FIG. 2B and the plurality of layers 170. The adhesion promoting layer can be formed from any suitable material that promotes the adhesion or retention of one or more of the coating layers, such as silane, pyrolytic carbon, parylene and the like.

In some embodiments, materials that promote the adhesion of an outer coating layer, such as coating layer 142 in FIG. 2A, to the wall of a body vessel. Alternatively, materials that promote adhesion to a portion of the body upon implantation therein can be incorporated into the coating layer 142. Chemical or biological modifications of the device surface or coating layers can also enhance adhesion between an implantable medical device and the surrounding host tissue. For example, devices have been coated with a substance to enhance the healing process and/or adhesion of the device to the host tissue. In one approach, implantable medical devices can permit infiltration by specific desirable tissue cells. One type of tissue infiltration involves the process known as "endothelialization", i.e., migration of endothelial cells from adjacent tissue onto or into the device surface. Methods for promoting endothelialization can include applying a porous coating to the device which allows tissue growth into the interstices of the implant surface (see, e.g., WO 96/37165A1). Also, an electrically charged or ionic material (e.g., fluoropolymer) can be applied to a portion of the tissue-contacting surface of the device or device coating (see, e.g., WO 95/19796A1; J. E. Davies, in Surface Characterization of Biomaterials, B. D. Ratner, ed., pp. 219-234 (1988); and U.S. Pat. No. 5,876,743). Biocompatible organic polymers (e.g., polymers substituted with carbon, sulfur or phosphorous oxyacid groups) can be added to a coating layer or portions of the medical device frame to promote osteogenesis at the host-implant interface (see, e.g., U.S. Pat. No. 4,795,475), or coatings made from biological materials (e.g., collagen) can be used to enhance tissue repair, growth and adaptation at the implant-tissue interface (e.g., U.S. Pat. No. 5,002,583).

Taxane Agents

In one embodiment, the therapeutic agent is a taxane agent. One aspect of the present invention relates to methods of coating compositions including taxane agents, such as paclitaxel. Taxanes in general, and paclitaxel in particular, are therapeutic compounds considered to function as a cell cycle inhibitors by acting as an anti-microtubule agent, and more specifically as a stabilizer. As used herein, the term "paclitaxel" refers to a compound of the chemical structure shown as structure (1) below, consisting of a core structure with four fused rings ("core taxane structure," shaded in structure (1)), with several substituents.

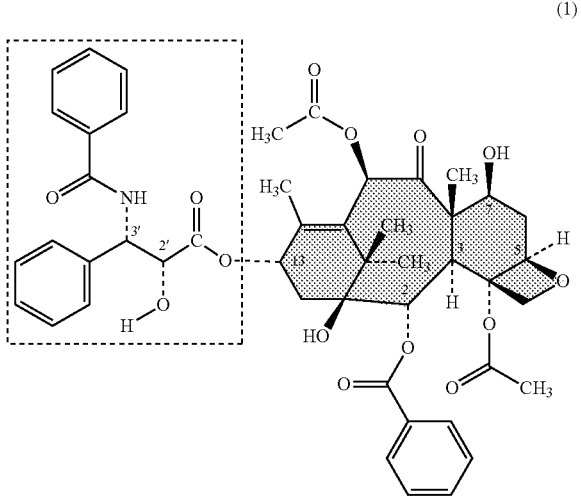

(1)

Other taxane analog or derivative compounds are characterized by variation of the paclitaxel structure (1). Preferred taxane analogs and derivatives core vary the substituents attached to the core taxane structure. In one embodiment, the therapeutic agent is a taxane analog or derivative including the core taxane structure (1) and the methyl 3-(benzamido)-2-hydroxy-3-phenylpropanoate moiety (shown in structure (2) below) at the 13-carbon position ("C13") of the core taxane structure (outlined with a dashed line in structure (1)).

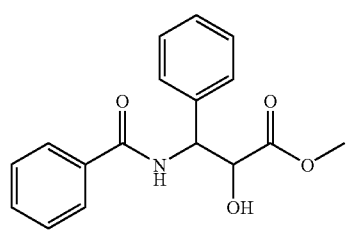

(2)

methyl 3-(benzamido)-2-hydroxy-3-phenylpropanoate

It is believed that structure (2) at the 13-carbon position of the core taxane structure plays a role in the biological activity of the molecule as a cell cycle inhibitor. Examples of therapeutic agents having structure (2) include paclitaxel (Merck Index entry 7117), docetaxol (TAXOTERE, Merck Index entry 3458), and 3'-desphenyl-3'-(4-nitrophenyl)-N-debenzoyl-N-(t-butoxycarbonyl)-10-deacetyltaxol.

A composition comprising a taxane compound can include formulations, prodrugs, analogues and derivatives of paclitaxel such as, for example, TAXOL (Bristol Myers Squibb, New York, N.Y.) Other representative examples of taxane compounds, including paclitaxel derivatives or analogues, that can be used as therapeutic agents are disclosed in copending application publication number 2008/0020013, published Jan. 24, 2008, the contents of which are incorporated by reference.

Solid Forms of Taxane Agent Compositions

The taxane agent can include one or more types of taxane agent(s). Taxane agent molecules having the same molecular structure may be arranged in different solid forms. Taxane agent molecules can exist in solvated or non-solvated solid forms that can be characterized and differentiated by one or more physical properties, including the rate of dissolution in various elution media (e.g., cyclodextrin or porcine serum) prior to implantation. Typically, taxane agents in a solvated solid form dissolve more slowly in an aqueous environment, for example in blood, than non-solvated solid forms, but are less durable than the non-solvated solid forms. Once dissolved, the taxane agent molecules having identical molecular structures but originating from different solid forms are indistinguishable in solution.

In one embodiment, the taxane agent is paclitaxel. Solid forms of paclitaxel at room temperature include: amorphous paclitaxel ("aPTX"), dihydrate crystalline paclitaxel ("dPTX") and anhydrous crystalline paclitaxel. These different solid forms of paclitaxel can be characterized and identified using various solid-state analytical tools, for example as described by Jeong Hoon Lee et al., "Preparation and Characterization of Solvent Induced Dihydrate, Anhydrous and Amorphous Paclitaxel," Bull. Korean Chem. Soc. v. 22, no. 8, pp. 925-928 (2001), incorporated herein by reference. For example, amorphous and dihydrate taxane solid forms may be readily identified and differentiated by visual appearance and elution rates. The dihydrate taxane solid form typically has an opaque white color, while the amorphous dihydrate taxane solid form typically has a clear transparent appearance. In addition, the presence of different solid forms of the taxane agent in a medical device coating can be identified and quantified by contacting the coating with an elution medium that selectively dissolves one solid form more readily than a second solid form. In solution with an elution medium, such as porcine serum or blood, the presence of the taxane agent can be identified, for example by using ultraviolet (UV) spectroscopy or high pressure liquid chromatography (HPLC). In certain elution media such as porcine serum, the solvated taxane agent structures dissolve more slowly than the non-solvated solid forms. Non-solvated solid forms include amorphous or anhydrous solid forms.

U.S. Pat. No. 6,858,644, filed Nov. 26, 2002 by Benigni et al. ("Benigni"), teaches a crystalline solvate comprising paclitaxel and a solvent selected from the group consisting of dimethylsulfoxide, N,N'-dimethylformamide, N,N'-dimethylacetamide, N-methyl-2-pyrrolidone, 1,3-dimethyl-2-imidazolidinone, 1,3-dimethyl-3,4,5,6-tetrahydro-2-(1H)-pyrimidinone, and acetonitrile and combinations thereof. However, Benigni does not describe implantable device coatings comprising crystalline paclitaxel forms with different elution rates. Benigni discloses various solid forms of paclitaxel, including a first solid form reported as a highly water insoluble crystalline, granular, solvent-free form. The first solid form is substantially non-hygroscopic under normal laboratory conditions (relative humidity (RH) approximately 50-60%; 20-30.degree. C.). However, when contacted with an atmosphere having a relative humidity greater than about 90%, or in aqueous suspensions, dispersions or emulsions, the first paclitaxel solid form reportedly converts (as a function of time, temperature, agitation, etc.) to a thermodynamically more stable second solid form. The second solid form is described as a trihydrate orthorhombic form having six water sites per two independent paclitaxel molecules (one paclitaxel "dimer"). These hydrated crystals reportedly present a fine, hair-like appearance and are even less water soluble than the first solid form. The second solid form is reportedly formed in aqueous suspensions or through crystallization from aqueous solvents in the presence of a large excess of water. This form is also disclosed in patent application EP 0 717 041, which describes the second solid form as being characterized by single crystal X-ray diffraction studies as being orthorhombic, with unit cells containing two crystallographically independent molecules of paclitaxel associated with hydrogen bonds to form a "dimer". Mastropaolo, et al. disclosed a crystalline solvate of paclitaxel obtained by evaporation of solvent from a solution of TAXOL™ in dioxane, water and xylene. Proc. Natl. Acad. Sci. USA 92, 6920-24 (July, 1995). This solvate is indicated as being unstable, and, in any event, has not been shown to effect purification of crude paclitaxel. The thin plate-like crystals are reported to contain five water molecules and three dioxane molecules per two molecules of paclitaxel. None of these references describe a durable taxane coating having an elution profile that can be altered by treatment of a medical device coating to vary the solid form composition of the coating.

The solvated solid forms of paclitaxel further include water molecules to form a solvated solid form, such as dihydrate paclitaxel (paclitaxel.2H$_2$O). The molar ratio between the taxane agent and the waters of hydration in a solvated solid form may include integer ratios as well as non-integer ratios, such as 2.2H$_2$O per paclitaxel water molecules. Preferably, the solvated solid form comprises a molar ratio of about 1.0 to 5.0 water molecules per molecule of taxane agent, including ratios 1.2, 1.3, 1.4, 1.5, 1.6, 1.7, 1.8, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 and 5.0, and higher, water molecules of hydration per molecule of taxane agent in the solvated solid form.

Figure 3A:
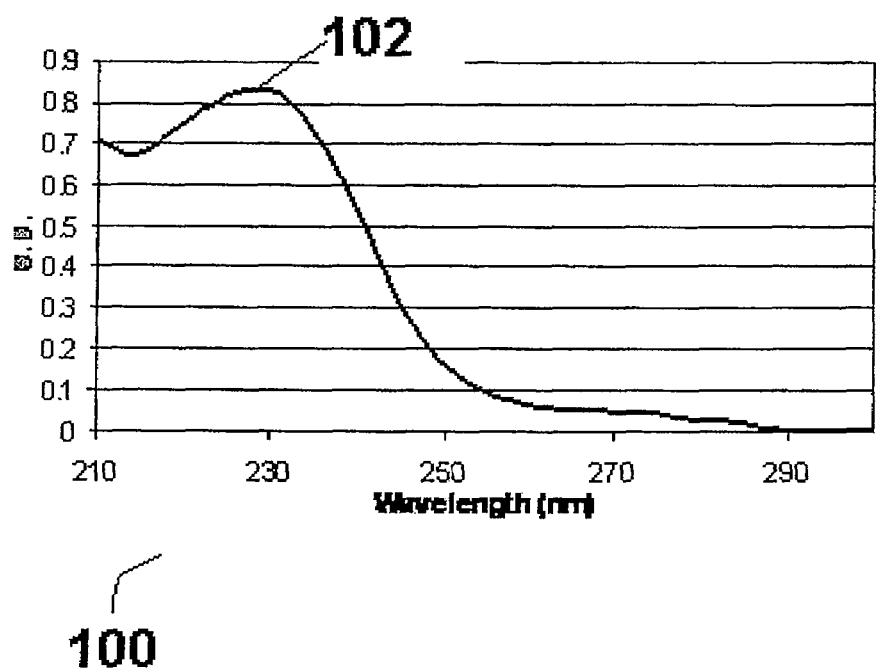
FIG. 3A shows a UV-Visible Spectra for paclitaxel in ethanol.

The presence of a taxane agent in a coating structure can be identified by detecting the core taxane structure, for example by ultraviolet detection methods. For example, samples of the coating may be destructively tested by dissolving the coating in any suitable elution medium that permits measurement of a characteristic peak of the taxane agent in solution in an ultraviolet (UV) spectrum of the taxane agent in the solution. The characteristic peak is preferably associated with the core taxane structure. Methanol and ethanol are preferred examples of suitable solvents. FIG. 3A shows an ultraviolet (UV) spectrum 100 (Agilent In-line UV Spectrophotometer) of paclitaxel in ethanol, obtained from a 25.67 micromolar solution of paclitaxel in ethanol. Paclitaxel provides a characteristic peak at 227 nm (102) indicative of the presence of the core taxane structure of paclitaxel in the solution. Taxane agents can be identified from a UV spectrum of the elution medium characterized by the characteristic peak at about 227 nm, which can be correlated to the presence of the taxane agent in the solution, regardless of the solid form from which the taxane molecule originated.

Different solid forms of taxane agents in medical device coatings can have identical molecular structures, but differ in the arrangement of the taxane molecules in the coating. Various solid forms of the taxane agent can be identified and differentiated on the basis of one or more physical properties including melting point, solubility and appearance. In addition, various other analytical methods can be used to identify different solid forms of the taxane agents, including vibrational spectroscopy (including Raman or Infrared Spectra), solubilities, melting points, X-ray Diffraction (XRD), $^{13}$C Nuclear Magnetic Resonance (NMR), and Temperature Programmed Desorption (TPD)).

Different solid forms of the taxane agent (including amorphous, anhydrous or dihydrate forms) can be formed by dissolving the solid taxane agent, typically obtained in the anhydrous form, in different solvents, as described below. These three solid forms of paclitaxel can be prepared and identified by the methods described in J. H. Lee et al, "Preparation and Characterization of Solvent Induced Dihydrated, Anhydrous and Amorphous Paclitaxel," *Bull. Korean Chem. Soc.*, v. 22, no. 8, pp. 925-928 (2001), which is incorporated herein by reference.

Figure 3B:
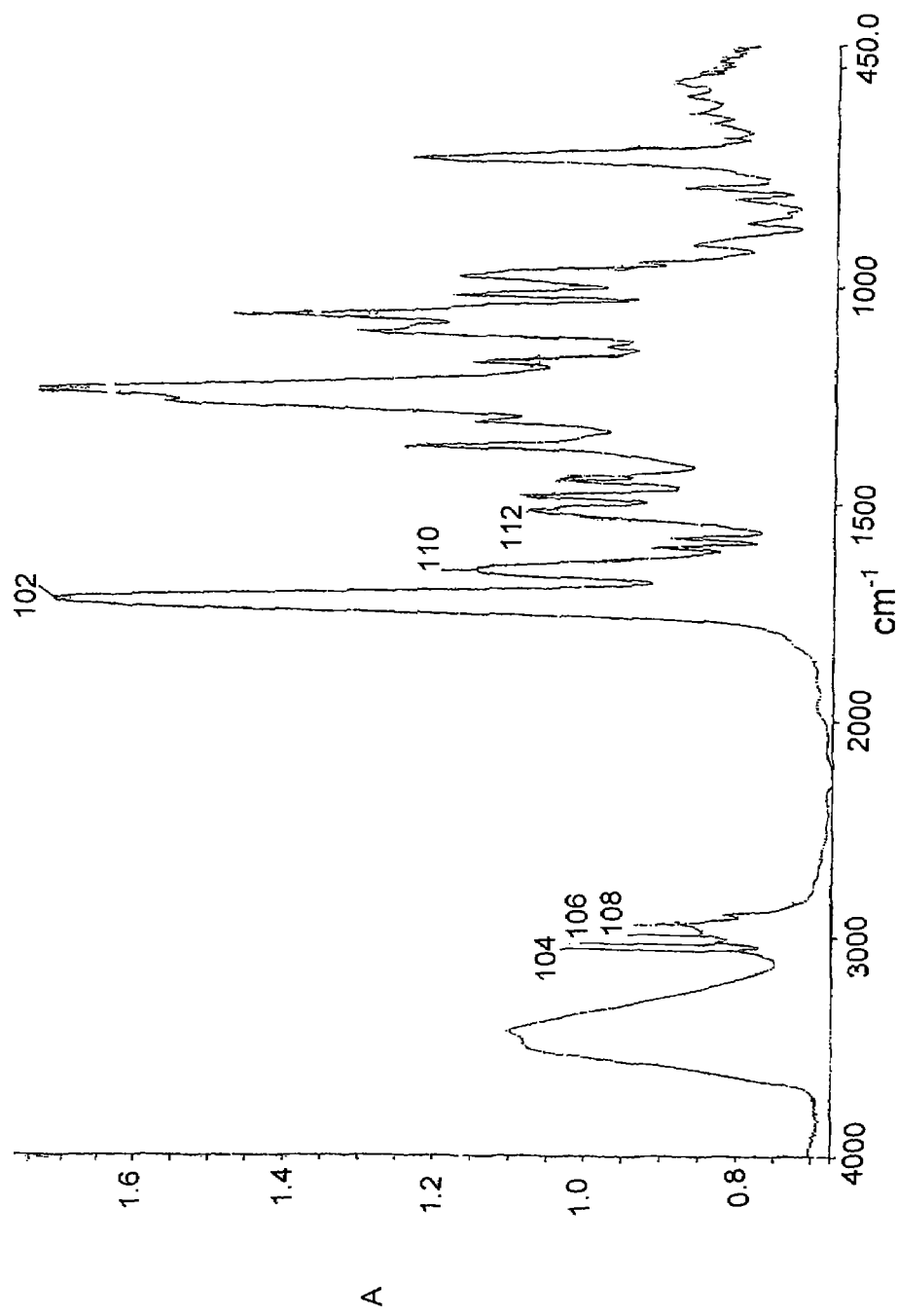
FIG. 3B shows an infrared spectrum of a first solid form of paclitaxel.

In one embodiment, medical devices comprising an amorphous taxane agent, such as amorphous paclitaxel ("aPTX"), are provided. Bulk amorphous paclitaxel can be prepared by dissolving the taxane agent in any suitable aprotic organic solvent, preferably in methylene chloride (dichloromethane), followed by removal of the solvent to leave an amorphous solid. Chloroform can also be used as the organic solvent. For example, amorphous taxane agent can be formed by first dissolving the solid taxane agent in dichloromethane, followed by crystallization at and evaporation of the dichloromethane and subsequent vacuum drying of the sample. Desirably, the synthesis method is carried out in a low humidity environment (preferably below about 40% relative humidity, more preferably below about 30% and most preferably below about 20% relative humidity or less), and at about 23° C. FIG. 3B shows an infrared vibrational spectrum of an amorphous paclitaxel prepared via the method of Example 1. The spectrum of amorphous paclitaxel 100 includes a single broad peak at about 1723 cm$^{-1}$ (102), as well as the following other characteristic peaks: 3064 cm$^{-1}$ (104), 3029 cm$^{-1}$ (106), 2942 cm$^{-1}$ (108), 1650 cm$^{-1}$ (110), and 1517 cm$^{-1}$ (112). The melting points of the amorphous paclitaxel samples prepared according to Example 1 were about 190° C.-210° C. An amorphous taxane agent can be identified by the presence of a single broad peak between about 1700-1740 cm$^{-1}$ in the infrared spectrum, typically at about 1723 cm$^{-1}$. The amorphous taxane agent was found to be more soluble in porcine serum than the dihydrate taxane agent, but less soluble than the anhydrous taxane agent.

Figure 3C:
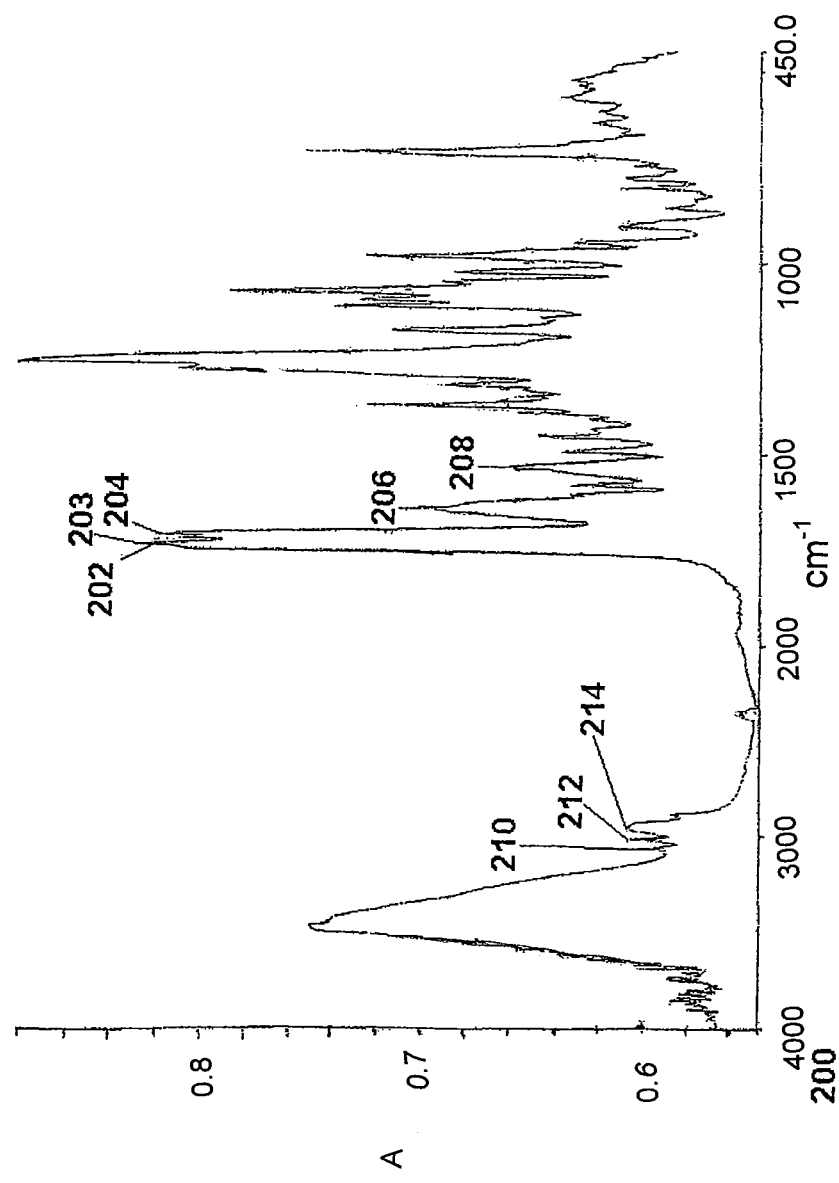
FIG. 3C shows an infrared spectrum of a second solid form of paclitaxel.
Figure 3D:
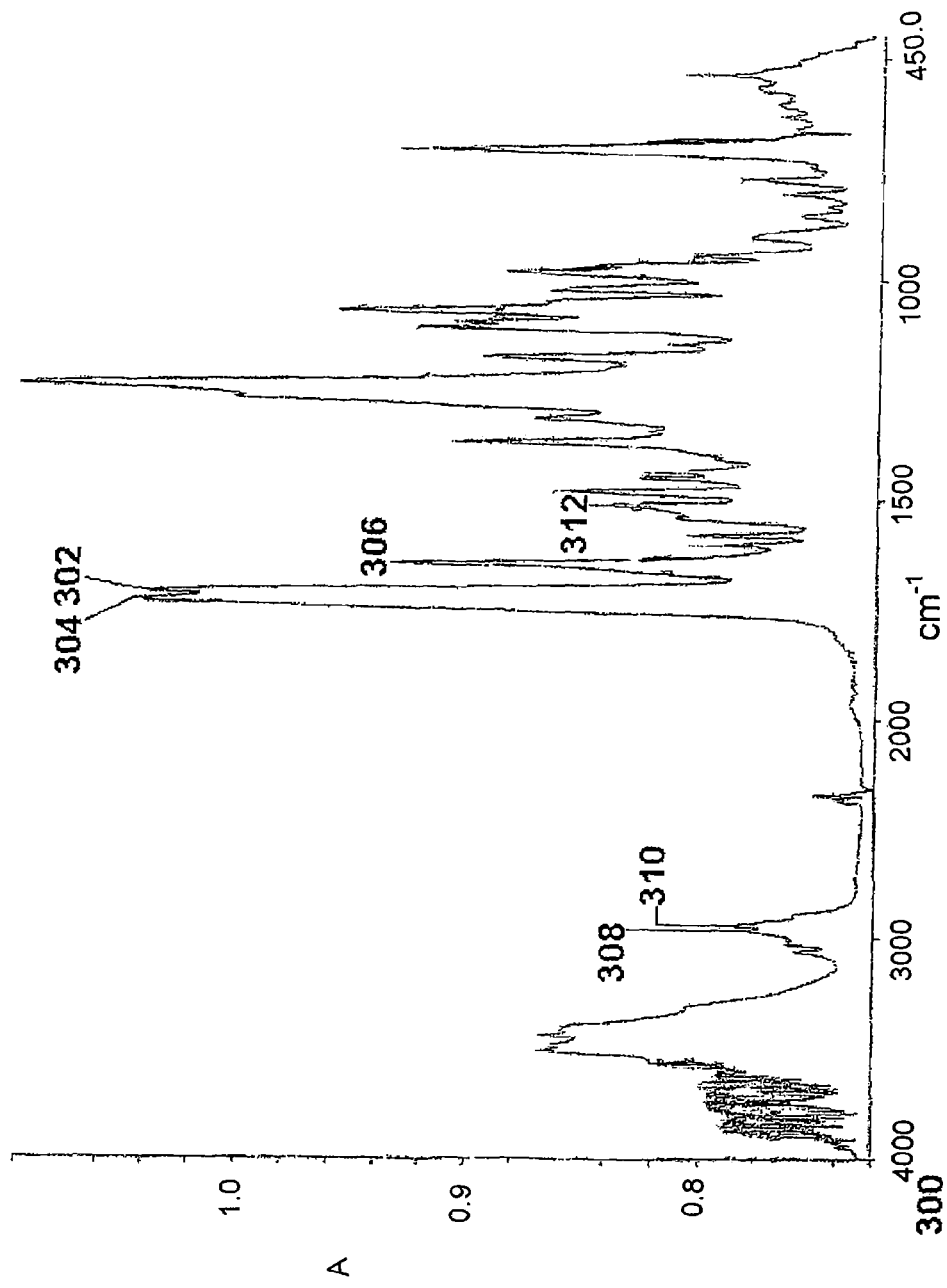
FIG. 3D shows an infrared spectrum of a third solid form of paclitaxel.

Another embodiment provides medical devices comprising an anhydrous taxane agent, such as anhydrous paclitaxel. Anhydrous taxane agents preferably contain less than about 1.00% water (more preferably less than about 0.60%, 0.55% or 0.50% water), as measured by Karl Fischer analysis. Bulk samples of anhydrous taxane agent can be prepared by dissolving a taxane agent such as paclitaxel in any suitable alcohol-based solvent, followed by evaporation of the solvent to leave an crystalline solid. Typically, the taxane agent is first dissolved in a methanol solvent, followed by the gradual addition of hexane to the solution. For example, as described in more detail in Example 1, anhydrous taxane agent can be formed by first dissolving paclitaxel in methanol to form a solution, followed by addition of hexane to the solution and subsequent evaporation of the methanol and hexane. Acetone, ethyl acetate or diethyl ether are also suitable solvents for combination with hexane in forming the anhydrous solid form of a taxane agent. The anhydrous paclitaxel prepared according to Example 1 was characterized by Infrared Spectrophotometry. FIG. 3D shows an infrared vibrational spectrum of an anhydrous paclitaxel prepared according to the method of Example 1. The spectrum of anhydrous paclitaxel 300 includes a pair of peaks between about 1700-1740 cm$^{-1}$, typically two peaks at about 1714 cm$^{-1}$ (302) and about 1732 cm$^{-1}$ (304), as well as the following other characteristic peaks: 3065 cm$^{-1}$ (308), 2944 cm$^{-1}$ (310), 1646 cm$^{-1}$ (306), and 1514 cm$^{-1}$ (312). The melting points of the anhydrous paclitaxel samples prepared according to Example 1 were about 220° C.-221° C. The anhydrous taxane agent was found to be more soluble in porcine serum than the amorphous taxane agent, and significantly more soluble than the dihydrate taxane agent.

Another embodiment provides medical devices comprising dehydrate paclitaxel. Bulk samples of dihydrate paclitaxel can be prepared by dissolving the taxane agent in any suitable alcohol-based solvent, followed by evaporation of the solvent to leave a crystalline solid. Typically, the taxane agent is first dissolved in a methanol or ethanol solvent, followed by the gradual addition of water to the solution. Specifically, bulk dihydrate taxane agent may be prepared by a multi-step process: (1) first, dissolving a solid anhydrous taxane agent in methanol to form a solution, followed by (2) adding water to the solution in a step-wise manner, followed by (3) crystallization. The water is preferably added very slowly, in a drop-by-drop manner, waiting for solution to become clear before the addition of the next drop of water, until the solution includes 80% v/v methanol and 20% v/v water. The dihydrate taxane agent can be collected by filtration and vacuum evaporation of the methanol and water. Desirably, the synthesis method is carried out in a high humidity environment (preferably at least about 20% relative humidity, more preferably about 40% or greater relative humidity), and at temperatures of about 23° C. or higher. Alternatively, studies have reported formation of paclitaxel dihydrate by incubation of anhydrous paclitaxel in water for 24 hours at 25° C. See, e.g., R. T. Liggins et al., "Solid-State Characterization of Paclitaxel," *Journal of Pharmaceutical Sciences*, v. 86, No. 12, p. 1461 (December 1997). The vibrational spectrum of the dihydrate paclitaxel prepared according to Example 1 may be obtained by Infrared Spectrophotometry. FIG. 3C shows an infrared vibrational spectrum of a dihydrate paclitaxel prepared according to the method of Example 1. The spectrum of dihydrate paclitaxel 200 includes three or more peaks between about 1700-1740 cm$^{-1}$, typically three peaks at about 1705 cm$^{-1}$ (204), about 1716 cm$^{-1}$ (203) and about 1731 cm$^{-1}$ (202), as well as the following other characteristic peaks: 3067 cm$^{-1}$ (210), 3017 cm$^{-1}$ (212), 2963 cm$^{-1}$ (214), 1639 cm$^{-1}$ (206), and 1532 cm$^{-1}$ (208). The melting points of the dihydrate paclitaxel samples prepared according to Example 1 were about 209° C.-215° C. Dehydration of dihydrate paclitaxel has been reported during heating at a rate of 10° C./min over a temperature range of between about 35° C. and about 100° C. measured by DSC (with peaks observed at about 50° C. and 72° C.), and between about 25° C. and about 85° C. measured by Thermogravimetric Analysis (TGA), with lower temperatures reported at slower heating rates. R. T. Liggins et al., "Solid-State Characterization of Paclitaxel," *Journal of Pharmaceutical Sciences*, v. 86, No. 12, pp. 1458-1463, 1461 (December 1997) ("Liggins"). The dihydrate paclitaxel has been reported to not show weight loss or evidence of dehydration when stored for several weeks when stored at 25° C. at 200 torr. Liggens et al., page 1461. The solubility of the bulk sample of dihydrate taxane agent may be measured in various elution media to obtain a dihydrate control elution profile. The elution profile of a taxane agent measure in the elution media may be compared to the dihydrate control elution profile to identify the amount of dihydrate solid form present in a taxane agent coating to identify the amount of the dihydrate present in the coating by comparison with the dihydrate control elution profile.

The presence of a single peak between 1700-1740 cm$^{-1}$ indicates the presence of an amorphous taxane therapeutic agent solid form, the presence of three or more peaks between 1700-1740 cm$^{-1}$ indicates the presence of the dihydrate taxane therapeutic agent solid form, and the presence of two peaks between 1700-1740 cm$^{-1}$ indicates the presence of the anhydrous taxane therapeutic agent solid form.

Suitable solvent systems for the synthesis of amorphous, dihydrate and anhydrous taxane therapeutic solid forms, as well as characteristic melting point ranges and infrared spectrum peaks useful in identifying each solid form, are provided in Table 1. Other solvent systems can also be used to form one or more of the taxane solid forms described herein, and other IR peaks can be used to identify the type(s) of solid forms present in a taxane agent solid sample.

TABLE 1

Preparation and Identification of Taxane Solid Forms

| | Desired Taxane Solid Form | | |
|---|---|---|---|
| | Amorphous | Anhydrous | Dihydrate |
| Solvent: | Dichloromethane | Methanol/Hexane | Methanol/Water |
| Melting Point: | 190-210° C. | 220-221° C. | 209-215° C. |
| Characteristic IR peaks: | Single peak between 1700-1740 cm$^{-1}$ | Two peaks between 1700-1740 cm$^{-1}$ | Three or more peaks between 1700-1740 cm$^{-1}$ |
| | 3064 cm$^{-1}$ (104), 3029 cm$^{-1}$ (106), 2942 cm$^{-1}$ (108) | 3065 cm$^{-1}$ (308), 2944 cm$^{-1}$ (310) | 3067 cm$^{-1}$ (210), 3017 cm$^{-1}$ (212), 2963 cm$^{-1}$ (214) |
| | 1650 cm$^{-1}$ (110) 1517 cm$^{-1}$ (112) | 1646 cm$^{-1}$ (306) 1514 cm$^{-1}$ (312) | 1639 cm$^{-1}$ (206) 1532 cm$^{-1}$ (208) |

Differentiation of taxane solid states by vibrational spectroscopy can also be performed using Raman scattering. Raman scattering describes the phenomenon whereby incident light scattered by a molecule is shifted in wavelength from the incident wavelength. The magnitude of the wavelength shift depends on the vibrational motions the molecule is capable of undergoing, and this wavelength shift provides a sensitive measure of molecular structure. That portion of the scattered radiation having shorter wavelengths than the incident light is referred to as anti-Stokes scattering, and the scattered light having wavelengths longer than the incident beam as Stokes scattering. Raman scattering is a spectroscopic method useful for the detection of coatings, as the Raman spectra of different coatings or coating layers can be more distinct than the spectra obtained by direct light absorption or reflectance. For example, three Raman spectral traces are recorded as an average of 10 spectra of three solid paclitaxel coatings on a stainless steel surface using a FT-Raman spectrometer, with excitation from a 532 nm laser with a power output of 8 mW. The three spectral traces correspond to the dihydrate, anhydrous and amorphous paclitaxel samples. Each spectral trace is collected over a 10 second integration each (total acquisition time of 100 seconds), using an air objective (100×, NA=0.9). Differences in the characteristic vibrational peaks can be used to differentiate the dihydrate, anhydrous and amorphous forms of the solid paclitaxel. Examples of such traces may be found in U.S. Publication Number 20070212394, published Sep. 13, 2007, the contents of which are incorporated by reference. The characteristic vibrational peaks correspond to the infrared characteristic peaks discussed with respect to the infrared spectra of FIGS. 3B-3D, and include the peaks listed in Table 1. Most notably, the presence of a single peak between 1700-1740 $cm^{-1}$ indicates the presence of an amorphous taxane agent solid form, the presence of three or more peaks between 1700-1740 $cm^{-1}$ indicates the presence of the dihydrate taxane agent solid form, and the presence of two peaks between 1700-1740 $cm^{-1}$ indicates the presence of the anhydrous taxane agent solid form. Further details of methods allowing for the detection and differentiation of differing forms of taxane, including differing forms of paclitaxel, are disclosed in copending application publication number 2008/0020013, published Jan. 24, 2008, the contents of which are incorporated by reference.

The presence of different solid forms of the taxane agent in a medical device coating can preferably be identified by contacting the coating with an elution medium that selectively dissolves one solid form more readily than a second solid form. In solution with an elution medium, such as porcine serum or blood, the presence of the taxane agent can be identified, for example by using ultraviolet (UV) spectroscopy or high pressure liquid chromatography (HPLC).

Coating Configurations

The elution profile of a medical device can be altered by varying parameters such as the solid form(s) of taxane agent, including the ratio of solid form(s), the composition and/or thickness of the coating layers and the ratio of the taxane agent to the bioabsorbable elastomer. For example, the elution rate can be decreased by (1) increasing the weight ratio of the bioasborbable elastomer to the taxane agent, (2) increasing the relative thickness of a bioabsorbable elastomer coating layer to an adjacent underlying taxane agent coating layer, (3) decreasing the total amount of taxane agent in a coating layer, and (4) increasing the ratio of the solvated solid forms (for example, dihydrate paclitaxel).

For example, the amorphous paclitaxel is more soluble in porcine serum than the dihydrate paclitaxel, but less soluble than the anhydrous paclitaxel. Devices including coatings having a greater percentage of paclitaxel in the dihydrate from exhibit a slower release rate compared to similar devices where for of the paclitaxel is present in the amorphous or anhydrous forms. In certain embodiments, devices requiring slow release of paclitaxel after implantation may benefit from including paclitaxel in the dihydrate solid form. However, the amorphous solid form of paclitaxel is more durable than the dihydrate form of paclitaxel. Typically, a higher durability coating may be required for crimping a radially expandable coated medical device, packaging and transport of the coated medical device.

Methods of coating medical devices to obtain a required ratio of an amorphous solid form of taxane agent to a hydrated solid form of taxane agent are disclosed in copending patent application publication number 2008/0020013, published Jan. 24, 2008, the contents of which are incorporated by reference. Such methods include post-deposition treatment of a medical device coating comprising a taxane agent, or "conditioning" of the coating, performed to alter the solid form composition of taxane agent in the coating. Such conditioning techniques may also be applied after application of the bioabsorbable elastomer. In one embodiment, the coating is treated to convert at least a portion of the taxane agent to dihydrate form.

The coating layers comprising the bioabsorbable elastomer are preferably thick enough to provide a desired rate of release of the taxane agent, but thin enough to provide a desired level of durability of the overall coating. Increasing the thickness of the bioabsorbable elastomer or increasing the weight ratio of the bioabsorbable elastomer to the taxane agent can decrease the rate of elution measured in the elution profile. Desirably, the thickness of each layer comprising the taxane agent or the biodegradable elastomer is selected to provide a desired rate of release of the taxane agent for an intended use. However, if the thickness of a layer is too large, however, the durability of the coating may be decreased.

Preferably, a coating layer comprising a biodegradable elastomer has a greater amount of biodegradable elastomer by weight than the weight of taxane agent in an adjacent coating layer. For example, the total weight ratio of taxane agent to bioabsorbable elastomer in an adjacent layer is preferably about 1:1 to about 1:100, including ratios of 1:5, 1:10, 1:25, 1:50, and 1:75 (including all ratios therebetween), measured as a total weight ratio of an entire coating having one or more layers. In one embodiment, the weight ratio of the amount of taxane agent to bioabsorbable elastomer in an adjacent layer is about 1:1 to about 1:20.

In one embodiment, coating layers comprising the bioabsorbable elastomer include a negligible amount of the taxane agent, although alternative embodiments can include coating layers with a mixture of the taxane agent and the bioabsorbable elastomer. A coating layer comprising the bioabsorbable elastomer preferably contains less than about 10 µg, or more preferably less than about 5, 4, 3, 2, 1, 0.5, 0.25, 0.20, 0.15, 0.10, 0.05 or 0.01 µg, of the taxane agent per $mm^2$ of the total surface area of the coating layer.

A coating layer comprising a biodegradable elastomer polymer may include an amount of one or more biodegradable elastomer polymer(s) suitable to provide a desired elution rate. For instance, a coating layer may comprise 0.01, 0.05, 0.10, 0.50, 1.00, 5.00, 10.00, 15.00, or 20.00 µg/$mm^2$ of one or more biodegradable elastomer polymer(s) as a function of the area of the coating layer, including intervals of about 0.01 and 0.001 therebetween. The coating preferably includes at least one layer comprising between about 0.01-20.00 µg/$mm^2$, 0.05-5.00 µg/$mm^2$, and more preferably about 0.01-3.00 µg/$mm^2$ of a biodegradable elastomer polymer. The layer(s) comprising the biodegradable elastomer preferably do not contain a taxane agent. Most preferably, the coating includes one or more layer(s) consisting of one or more biodegradable elastomer polymer(s), or consisting essentially of one or more of the biodegradable elastomer polymer(s).

The thickness of the layer may be selected to provide a desired rate of release. Each layer comprising a therapeutic agent preferably has a thickness that is about 2 to 10 times greater than the thickness of an adjacent layer comprising a therapeutic agent. More preferably, the thickness of the bioabsorbable elastomer layer between about 2.0 and 10.0 times greater, preferably about 2.0 to about 5.0 times greater, and most preferably about 2.0 to about 3.0 times greater than the thickness of the therapeutic agent layer(s), including bioabsorbable elastomer layers between about 0.4 µm and about 20 µm. Preferably, the thickness of each taxane agent layer can be between about 0.5 µm and about 1.0 µm and the thickness of each bioabsorbable polymer layer is between about 1.0 µm and about 10.0 µm, including bioabsorbable polymer layer thicknesses of about 1.0, 1.5, 2.0, 2.5, 3.0, 3.5, 4.0, 4.5, 5.0, 5.5, 6.0, 6.5, 7.0, 7.5, 8.0, 8.5, 9.0 9.5 and 10.0 µm.

The coating can include any suitable number of layers. The thickness of the entire coating is preferably between about 0.2 µm and about 15 µm. Even more desirably, the thickness of the entire coating is between about 0.6 µm and about 10 µm. For example, for a coating having six layers comprising three layers of taxane agent interspersed in an alternating fashion with three layers of polymer, the total thickness of the coating layers would desirably be between about 1.5 µm to about 66.0 µm. Each of the layers can have the same or different thicknesses, with each polymer layer preferably being about 2 to about 10 times thicker than an adjacent layer of taxane agent.

The coating can include any suitable number of layers, but preferably includes 2 or more layers, including 2, 3, 4, 5, 6, 7, 8, 9, 10, 11 or 12 layer configurations. In one embodiment, the total thickness of the multi-layer coating on any given surface (e.g., luminal or abluminal) of the medical device is preferably between about 0.2 µm and about 75 µm, preferably between about 0.4 µm and about 50 µm. More preferably, the total thickness of the coating on the abluminal surface is between about 0.5 µm and about 10 µm. The coating may include coating layers consisting essentially of a taxane agent or a bioabsorbable elastomer, coating layers containing a mixture of a taxane agent and bioabsorbable elastomer, or any combination of these.

Biodegradable Elastomers

In one embodiment, the bioabsorbable elastomer is a polymer selected to provide a mechanically stable coating layer that readily recovers from deformation of the medical device without undesirable levels of irritation to surrounding tissue upon implantation. The bioabsorbable elastomer can include a hydrogel, an elastin-like peptide, a polyhydroxyalkanoates (PHA), polyhydroxybutyrate compounds, or combinations thereof. The bioabsorbable elastomer can be selected based on various design criteria, including the desired rate of release of the therapeutic agent and the degradation mechanism. In some embodiments, the bioabsorbable elastomer comprises one or more hydrolyzable chemical bonds, such as an ester, a desired degree of crosslinking, a degradation mechanism with minimal heterogeneous degradation, and nontoxic monomers.

The bioabsorbable elastomer may be a polyhydroxyalkanoate compound, a hydrogel, poly(glycerol-sebacate) or an elastin-like peptide. Desirably, the bioabsorbable elastomer includes a polyhydroxyalkanoate bioabsorbable polymer such as polylactic acid (poly lactide), polyglycolic acid (poly glycolide), polylactic glycolic acid (poly lactide-co-glycolide), poly-4-hydroxybutyrate, poly-3-hydroxybutyrate, chitosan, xanthan gum or a combination of any of these materials. In one embodiment, the taxane agent is initially enclosed by the coating or other portions of the medical device, and does not form a portion of the external surface area of the medical device prior to release of the therapeutic agent.

In one embodiment, the bioabsorbable elastomer comprises a poly-α-hydroxy acid, such as polylactic acid (PLA). PLA can be a mixture of enantiomers typically referred to as poly-D,L-lactic acid. Alternatively, the bioabsorbable elastomer is poly-L(+)-lactic acid (PLLA) or pol-D(−)-lactic acid (PDLA), which differ from each other in their rate of biodegradation. PLLA is semicrystalline. In contrast, PDLA is amorphous, which can promote the homogeneous dispersion of an active species. Unless otherwise specified, recitation of "PLA" herein refers to a bioabsorbable polymer selected from the group consisting of: PLA, PLLA and PDLA. In various embodiments embodiment, the molecular weight of the bioabsorbable elastomer is about 50-500 kDa, about 60-250 kDa, or about 75-120 kDa.

The bioabsorbable elastomer can also desirably comprise polyglycolic acid (PGA). Polyglycolic acid is a simple aliphatic polyester that has a semi-crystalline structure, fully degrades in 3 months, and can undergo strength loss within about 1 month after implantation in the body. Compared with PLA, PGA is a stronger acid and is more hydrophilic, and thus more susceptible to hydrolysis. PLA is generally more hydrophobic than PGA, and undergoes a complete mass loss in 1 to 2 years.

The bioabsorbable elastomer can also be a polylactic glycolic acid (PLGA), or other copolymers of PLA and PGA. The properties of the copolymers can be controlled by varying the ratio of PLA to PGA. For example, copolymers with high PLA to PGA ratios generally degrade slower than those with high PGA to PLA ratios. PLGA degrades slightly faster than PLA. The process of lactic acid hydrolysis can be slower than for the glycolic acid units of the PLGA co-polymer. Therefore, by increasing the PLA:PGA ratio in a PLGA copolymer generally results in a slower rate of in vivo bioabsorption of a PLGA polymer.

A summary of the properties of some desirable bioabsorbable elastomer polymers are shown below in Table 2.

TABLE 2

| Polymer | Crystallinity | Degradation Rate (depends on molecular weight of polymer) | Typical Applications |
|---|---|---|---|
| PGA | High Crystallinity | 2-3 months | Suture, soft anaplerosis |
| PLLA | Semi-crystalline | >2 years | Fracture fixation, ligament |
| PDLA | Amorphous | 12-16 months | Drug delivery system |
| PLGA | Amorphous | 1-6 months (depends on ratio of LA to GA) | Suture, fracture fixation, oral implant, drug delivery |

Cross-linked polymers of glycerol and sebacic acid can also be used as the bioabsorbable elastomer, such as a poly-4-hydroxybutyrate (P4HB) or poly(glycerol-sibacate) (PGS). PGS can be prepared by the polycondensation of glycerol and sebacic acid to yield an elastomer. PGS can be formed with any suitable ratio of glycerol:sebacic acid. Preferably, the bioabsorbable elastomer is a PGS with 1:1 glycerol:sebacic acid ratio, which is largely insoluble in water and swells about 2% after soaking in water for 24 hours, can have a cross-linking density of about 38 mol/m$^3$ and two DSC melting temperatures at 5.23° C. and 37.62° C. Accordingly, the 1:1 PGS polymer is completely amorphous at 37° C. within the body. The preparation and characterization of a 1:1 glycerol:sebacic acid PGS bioabsorbable elastomer is described in Y. Wang et al., "A tough biodegradable elastomer," *Nature Biotechnology*, 20, 602-606 (2002), which is incorporated herein by reference. Briefly, the 1:1 PGS can be prepared in an uncrosslinked prepolymer that can be melted into a liquid and dissolved in common organic solvents including 1,3-dioxolane, tetrahydrofuran, ethanol, isopropanol and N,N-dimethylformamide. A mixture of NaCl particles and an anhydrous 1,3-dioxolane prepolymer can be poured into a PTFE mold. The polymer can be cured in the mold in a vacuum oven at 120° C. and 100 mtorr, and a porous scaffold can be obtained after salt leaching with deionized water. Desirably, the PGS bioabsorbable elastomer has a strain to failure property similar to that of arteries and veins (e.g., up to about 260%) and larger than tendons (up to about 18%). Furthermore, the weight of PGS can remain substantially unchanged after soaking 24 hours in an aqueous environment, and the mechanical properties can remain largely unchanged compared to the dry polymer. Y. Wang et al. reported that 1:1 PGS degrades about 17% after 60 days in PBS solution at 37° C., as measured by change in weight; subcutaneous implantation of the 1:1 PGS in rats lead to complete absorption of the polymer in 60 days (Y. Wang et al., "A tough biodegradable elastomer," *Nature Biotechnology*, 20, 602-606 (2002)). Data indicated that mechanical strength of the 1:1 PGS decreases linearly with mass loss, suggesting a surface erosion mechanism (Y. Wang et al., "A tough biodegradable elastomer," *Nature Biotechnology*, 20, 602-606 (2002)).

Alternative ratios of glycerol:sebacic acid can also be prepared, including a 2:3 PGS ratio polymer described by M. Nagata et al., "Synthesis, characterization, and enzymatic degradation of network aliphatic copolyesters," *J. Polym. Sci. Part A: Polym. Chem.*, 37, 2005-2011.

Coating Methods

In another embodiment, methods of coating a surface of an implantable medical device are provided. The coating may be applied to a surface of an implantable medical device by any suitable method. Coating layers may be applied in sequential fashion to the surface of the medical device. Preferably, a layer comprising a taxane agent is first applied over the surface of the implantable medical device, and another layer comprising a biodegradable elastomer is applied over the taxane agent. The coating layers can be deposited on the surface of an implantable medical device or be locally deposited within holes or wells in the surface of the medical device. Three preferred methods for applying coating layers are described herein: (1) spray gun coating, (2) ultrasonic spray coating and (3) electrostatic spray coating.

In all three methods, a coating layer comprising a taxane agent can be formed by applying a first solution of the taxane agent to the surface of the medical device. In one embodiment, the first solution consists essentially of the taxane agent and a volatile solvent, and does not contain the bioabsorbable elastomer. In one embodiment, the therapeutic agent is paclitaxel and the solvent is ethanol or methanol. For example, a solution of about 0.5-5.0 mM paclitaxel in ethanol may used, preferably solutions of 0.7 mM, 1.2 mM paclitaxel in ethanol. Other therapeutic agents and solvents may also be used in solutions at concentrations permitting desirable deposition rates forming coatings with desired durability.

The spray coating can be performed by any suitable coating technique, but typically includes the step of dissolving the taxane agent in a suitable solvent and spraying the resulting solution onto the surface of the medical device. Changing the solvent(s) in the solution can change the solid forms of the resulting taxane agent deposited on a medical device. To deposit a coating of a dihydrate taxane agent, a recrystallized dihydrate taxane can be dissolved in a suitable organic alcohol solvent, such as methanol. To deposit a coating layer comprising a mixture of dihydrate and amorphous taxane solid forms, the taxane is preferably dissolved in a spray solvent comprising a mixture of water and a protic solvent such as methanol. Importantly, varying the ratio of water to methanol and/or the concentration of the taxane in the spray solvent comprising the taxane typically changes the composition of the resulting coating layer that is spray deposited. Generally, increasing the amount of methanol in the spray solution results in a coating layer with a higher proportion of amorphous taxane. Further details regarding the parameters used to apply taxane coating may be found in co-pending application publication number 2008/0020013, published Jan. 24, 2008, the contents of which are incorporated by reference.

After the application of the taxane agent, another layer comprising a bioabsorbable elastomer material can be dissolved in a solvent and then sprayed onto a layer of therapeutic agent that was previously deposited on the medical device. In one embodiment, the polymer is PLA and the solvent is acetone. In another embodiment, the solvent is tetrahydrofuran (THF). In another embodiment, about 0.1-7.0 g/L of PLA in acetone is used. In yet another embodiment, about 2.5-6.5 g/L n acetone is used. In another embodiment, about 5.0 g/L of PLA in acetone is used.

In certain embodiments, the bioabsorbable elastomer is applied to the layer of taxane agent in a manner so as to prevent, or at least reduce, conversion of the dihydrate form to the amorphous form of paclitaxel. Such conversion can occur if the bioabsorbable elastomer, such as PLA, is applied using a solvent, such as dichloromethane (DCM), that dissolves dihydrate paclitaxel, causing amorphous paclitaxel to form upon drying. In one embodiment, dissolution is limited by choosing coating conditions that result in the evaporation of most of the DCM solvent before the coating spray reaches the paclitaxel layer. This may be achieved by increasing the spray nozzle distance from the target and controlling the temperature and humidity to ensure sufficient evaporation of the solvent before the spray reaches the target.

Conversion to the amorphous form can also be limited by adding a second spray line to deliver a water/methanol mixture to the target. Delivery of water to the surface of the target can felicitate conservation of dissolved dihydrate back to the dihydrate form. Inclusion of methanol in the spray reduces repulsion between the water and DCM sprays. Such repulsion can result in non-uniform coating.

In another embodiment, a low molecular weight bioabsorbable elastomer that is soluble in water is coated onto the paclitaxel layer. In another embodiment, after forming an initial coating of low molecular weight material, a layer of higher molecular weight bioabsorbable elastomer in coated onto the device using a solvent such as DCM.

In another embodiment, the bioabsorbable elastomer is applied is applied using a solvent, such as acetone or THF, that is less likely to dissolve the dihydrate form. In yet another embodiment, the bioabsorbable elastomer is applied using a solvent-free method, such as melt deposition.

In another embodiment, the implantable device is treated, or conditioned, after application of the bioabsorbable elastomer to convert at least a portion of the taxane agent to the dihydrate form. In yet another embodiment, the implantable device is treated, or conditioned, after application of the bioabsorbable elastomer and after crimping to convert at least a portion of the taxane agent to the dihydrate form. Further details regarding methods of converting taxane agent forms after coating are disclosed in copending patent application publication number 2008/0020013, published Jan. 24, 2008. The device may be soaked in water or exposed to a high humidity environment so that water permeates through the bioabsorbable elastomer layer and converts a portion of the taxane agent to the dihydrate form. The duration of exposure to water is controlled to minimize uptake of water by the bioabsorbable elastomer and to control the amount of the dihydrate form. In one embodiment, a bioabsorbable elastomer that is less hygroscopic than the taxane agent is used. In other embodiments, degradation of the bioabsorbable elastomer is controlled by choosing a high molecular weight elastomer and/or by adjusting the thickness of the elastomer coating.

Each coating layer is preferably separately applied using an ultrasonic nozzle spray coating technique employing ultrasound to atomize the spray solution, to provide a smooth and uniform polymer coating. Preferably, the polymer coating is applied from an ultrasonic nozzle. A solution of about 2-4 g/L of a bioabsorbable elastomer such as PLA in a suitable solvent such as acetone or THF can be applied using an ultrasonic nozzle. Ultrasonic nozzles can be configured such that excitation of the piezoelectric crystals creates a transverse standing wave along the length of the nozzle. The ultrasonic energy originating from the crystals located in the large diameter of the nozzle body undergoes a step transition and amplification as the standing wave as it traverses the length of the nozzle. The ultrasonic nozzle can be designed so that a nodal plane is located between the crystals. For ultrasonic energy to be effective for atomization, the atomizing surface (nozzle tip) is preferably located at an anti-node, where the vibration amplitude is greatest. To accomplish this, the nozzle's length must be a multiple of a half-wavelength. Since wavelength is dependent upon operating frequency, nozzle dimensions can be related to operational frequency. In general, high frequency nozzles are smaller, create smaller drops, and consequently have smaller maximum flow capacity than nozzles that operate at lower frequencies. The ultrasonic nozzle can be operated at any suitable frequency, including 24 kHz, 35 kHz, 48 kHz, 60 kHz, 120 kHz or higher. Preferably, a frequency of 60-120 kHz or higher is used to atomize the solution of the bioabsorbable elastomer to the greatest possible extent so as to promote the formation of a smooth, uniform coating. Power can be controlled by adjusting the output level on the power supply. The nozzle power can be set at any suitable level, but is preferably about 0.9-1.2 W and more preferably about 1.0-1.1 W. The nozzle body can be fabricated from any suitable material, including titanium because of its good acoustical properties, high tensile strength, and excellent corrosion resistance. Liquid introduced onto the atomizing surface through a large, non-clogging feed tube running the length of the nozzle absorbs some of the vibrational energy, setting up wave motion in the liquid on the surface. For the liquid to atomize, the vibrational amplitude of the atomizing surface can be maintained within a band of input power to produce the nozzle's characteristic fine, low velocity mist. Since the atomization mechanism relies only on liquid being introduced onto the atomizing surface, the rate at which liquid is atomized depends largely on the rate at which it is delivered to the surface. Therefore, an ultrasonic nozzle can have a wide flow rate range. The maximum flow rate and median drop diameter corresponding to particular nozzle designs can be selected as design parameters by one skilled in the art. Preferably, the flow rate is between about 0.01-2.00 mL/min, more preferably between about 0.05-1.00 and most preferably between about 0.05-0.07 mL/min. Preferred coating parameters for USD using a Sono-tek Model 8700-60 ultrasonic nozzle are provided in Table 3 below:

TABLE 3

Ultrasonic Spray Deposition Parameters for Sono-tek Model 8700-60

| Flow rate (mL/min) | Coating velocity (in/sec) | Rotation Speed (rpm) | Nozzle Power (watts) | Process Gas (psi) | Distance (mm) |
|---|---|---|---|---|---|
| 0.01-2 | 0.01-0.5 | 30-150 | 0.9-1.2 | 0.1-2.5 | 1-25 |

Alternatively, the taxane agent and bioabsorbable elastomer can be dissolved in a solvent(s) and sprayed onto the medical device using a conventional spray gun such as a spray gun manufactured by Badger (Model No. 200), an electrostatic spray gun, or most preferably an ultrasonic nozzle spray gun. Medical device coatings comprising a taxane agent may be applied to a surface of a medical device using a spray gun. The surface of the medical device can be bare, surface modified, or a primer coating previously applied to the medical device. In one embodiment, the coating applied to the surface consists essentially of the taxane agent, and is substantially free of polymers or other materials. The taxane agents, and optionally a polymer, can be dissolved in a solvent(s) and sprayed onto the medical device under a fume hood using a conventional spray gun, such as a spray gun manufactured by Badger (Model No. 200), or a 780 series spray dispense valve (EFD, East Providence, R.I.). Alignment of the spray gun and stent may be achieved with the use of a laser beam, which may be used as a guide when passing the spray gun over the medical device(s) being coated.

In one embodiment, the therapeutic agent is paclitaxel and the solvent is ethanol or methanol. For example, a solution of paclitaxel in ethanol described above is used. The distance between the spray nozzle and the nozzle size can be selected depending on parameters apparent to one of ordinary skill in the art, including the area being coated, the desired thickness of the coating and the rate of deposition. Any suitable distance and nozzle size can be selected. For example, for coating an 80 mm long stent, a distance of between about 1-7 inches between the nozzle and stent is preferred, depending on the size of the spray pattern desired. The nozzle diameter can be, for example, between about 0.014-inch to about 0.046-inch.

Varying parameters in the spray coating process can result in different solid forms of the taxane agent in a deposited coating. Spray coating parameters such as solvent system, fluid pressure (i.e., tank pressure), atomization pressure, ambient temperature and humidity. The solvent is desirably volatile enough to be readily removed from the coating during or after the spray coating process, and is preferably selected from the solvents discussed above for each solid form of a taxane agent.

Methods of coating amorphous taxane agents using a 780S-SS spray dispense valve (EFD, East Providence, R.I.) can comprise: dissolving solid paclitaxel in ethanol to form a solution, and spraying the solution onto a medical device with an atomization pressure of about 5-10 psi in an environment having a relative humidity of 30% or lower. In one embodiment, the spraying step is performed at a temperature of between about 65° F. and 75° F., and with a fluid pressure of between about 1.00 and 5.00 psi.

One or more coating layers may also be applied using an electrostatic spray deposition (ESD) process. The ESD process generally depends on the principle that a charged particle is attracted towards a grounded target. The solution that is to be deposited on the target is typically charged to several thousand volts (typically negative) and held at ground potential. The charge of the solution is generally great enough to cause the solution to jump across an air gap of several inches before landing on the target. As the solution is in transit towards the target, it fans out in a conical pattern which aids in a more uniform coating. In addition to the conical spray shape, the electrons are further attracted towards the metal portions of the target, rather than towards the non conductive base the target is mounted on, leaving the coating mainly on the target only.

Generally, the ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), incorporated herein by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

In one embodiment, the bioabsorbable elastomer (such as PLA) is dissolved in acetone. It is believed that the use of acetone as the solvent allows the bioabsorbable elastomer to be applied to a coating containing dihydrate paclitaxel without causing the dihydrate form to dissolve and reform other solid forms that are more soluble in an aqueous environment. In one embodiment, the presence of a bioabsorbable elastomer coating over a taxane agent layer including the dihydrate form results in an implantable device having a slower rate of elution of paclitaxel than a similar device not including the dihydrate form. In various embodiments, at least 10%, 20%, 30%, 40%, 50%, 60%, 70%, 80% or 90% of the taxane agent is present in the dihydrate form.

Coating Uniformity and Durability

The coatings are also preferably sufficiently durable to withstand percutaneous transcatheter deployment in a radially compressed state, which can include resistance to flaking, chipping or crumbling of the coating during crimping onto a catheter delivery system.

Desirably, coatings have sufficient durability to retain a desired amount of a taxane agent after manipulations typically associated with the manufacture and delivery of the medical devices to a desired point of treatment, and to function to release the therapeutic agent at the point of treatment at a desired rate. Durable coatings on medical device preferably resist flaking, pitting or delamination as a result of physical abrasion, compression, flexion, vibration, fluid contact, and fluid shear. For implantable vascular stents, coatings are desirably durable enough to maintain a substantially uniform coating during sterilization, radial compression by crimping onto a delivery catheter, and radial expansion within a blood vessel at a point of treatment.

The durability of a coating can be evaluated by weighing the medical device a first time immediately after coating, subjecting the coated medical device to physical forces typical of the manufacture and delivery process for an intended use (e.g., crimping, freezing, sterilization and the like), and then weighing the coated medical device a second time. A loss in weight between the first weighing and the second weighing could indicate the loss of portions of the coating to flaking or delamination. Preferably, durable coatings for implantable vascular stents loose no more than about 10 □g or about 20% of the coating weight or less before and after crimping. A durable coating preferably loses less than about 15%, more preferably between about 0-10%, most preferably between about 0% and 5% of the weight of the coating during the crimping process. Durable coatings are also substantially free of "webbing," or coating deposited over interstitial spaces between portions of a medical device.

Preferably, the coatings have a substantially uniform surface, without cracking or pitting. Desirably, coatings have a surface that retains surface uniformity and integrity upon sterilization and crimping. Various coating methods can be used to produce suitably smooth and durable coatings. Preferably, the top layer of a coating comprises a bioabsorbable elastomer. Substantially uniform and durable coatings can be deposited by spraying a solution of a taxane agent or bioabsorbable elastomer onto the abluminal surface of a medical device using conventional pressure gun, electrostatic spray gun or ultrasonic spray gun. The uniformity of a coating can be evaluated from optical and SEM images of the surfaces. Further details regarding method of applying a durable coating of a biodegradable elastomer, such as PLA, are disclosed in co-pending publication number 2007/0196423A1, published Aug. 23, 2007, the contents of which are incorporated by reference.

Such methods may include the application of one or more primer layers between the surface of the medical device and the taxane agent to adhere the taxane agent to the surface or enhance the durability of the coating. This layer may include, for example, silane, acrylate polymer/copolymer, acrylate carboxyl and/or hydroxyl copolymer, polyvinylpyrrolidone/vinylacetate copolymer, olefin acrylic acid copolymer, ethylene acrylic acid copolymer, epoxy polymer, polyethylene glycol, polyethylene oxide, pyrolytic carbon, polyvinylpyridine copolymers, polyamide polymers/copolymers polyimide polymers/copolymers, ethylene vinylacetate copolymer and/or polyether sulfones. The primer layer can have any suitable thickness, including between about 0.01 □m and 5.00 □m.

Taxane Agent Elution Profiles

Medical device coatings may be characterized by measuring the elution profile of the coating in a particular elution medium. An elution profile is a graph showing the rate at which the taxane agent is released from a coated medical device into an elution medium as a function of time the coating is in contact with an elution medium. Elution profiles may be used to identify particularly preferred coating configurations that provide a release of a therapeutic agent at a desired rate and/or for a desired period of time. Sustained release coatings characterized by a release of about 70-90% of the taxane agent from the coating over a period of about 15-20 days in porcine serum are particularly preferred for some applications. Desirably, the coatings are also configured to release a therapeutically effective dose of the taxane agent over a treatment period. The treatment period for restenosis may vary, but can be about 15 days for delivery of about 10-15 mg of a taxane agent to a portion of an arterial wall.

The amount of taxane agent released from coating into the elution medium, and the rate of release of the taxane agent from a coating, can be measured by any suitable method that allows for measurement of the release of the taxane agent with a desired level of accuracy and precision. The taxane agent in the coating can be determined by dissolving the coating in a suitable elution medium and subsequently detecting the amount of taxane agent in the elution medium. The taxane agent dissolved in the elution medium can be detected using any suitable technique. A suitable method, such as a spectrographic technique, permits measurement of a property of the test solution that can be correlated to the presence or concentration of the taxane agent analyte with a desired level of accuracy and precision. Various spectrographic measurements of the elution medium can be correlated with the amount of therapeutic agent removed from the medical device coating. Suitable spectrographic techniques for detecting the taxane agent in the elution medium include: UV absorption spectrum of a elution medium after contacting the medical device, use of an HPLC spectrophotometer with to a UV-VIS detector, or Liquid Chromatography paired with a Mass Spectrophotometer Detector. For example, taxane agents, such as paclitaxel, can be detected in a porcine serum elution medium using a UV-Visible Spectrophotometer. The detection of the therapeutic agent can be correlated to the amount of therapeutic agent that was present on the medical device surface prior to contacting the medical device with the solvent. When absorption spectroscopy is used to detect the presence of a therapeutic agent, such as in a test solution or solvent solution, the Beer-Lambert Correlation can be used to determine the concentration of a therapeutic agent in the solution. This correlation involves the linear relationship between optical density (absorbance) and concentration of an absorbing species. Using a set of standard samples with known concentrations, the correlation can be used to measure the optical density (O.D.) of the sample. A plot of concentration versus optical density (calibration plot) can then be used to determine the concentration of an unknown solution from its optical density. FIG. 3 shows a UV-Visible Spectra for 25.67 µM paclitaxel in an ethanol elution medium. The presence of paclitaxel and certain taxanes can be detected in the porcine serum based on the absorption at about 230 nm. Such data may be obtained from an apparatus such as the Agilent 8453 Photodiode Array UV-Vis Spectrophotometer. A calibration plot can be made by measuring the optical density of known concentrations of a therapeutic agent. Then, a coated medical device comprising an unknown amount of therapeutic agent can be placed in contact with the elution medium to dissolve the therapeutic agent at a desired rate, and subsequent detection of the optical density of the therapeutic agent in the elution medium can be correlated to the amount of therapeutic agent coated on or dissolved from the medical device coating.

The elution profile of a coated medical device can vary depending on the elution medium and conditions in which the therapeutic agent is released. A suitable elution medium solubilizes a taxane agent while allowing for subsequent measurement of the solubilized taxane agent in a manner that can be correlated to the amount of taxane agent in the coating. Preferably, substantially all of the taxane agent is removed from the medical device after contact with the elution medium for a desired period of time. The desired time period for elution should be long enough to permit adequate resolution in measurement of the release rate into the elution medium, but short enough not to require an undesirably long period of time to measure the total amount of the therapeutic agent in the coating.

The elution profile of a medical device coating can be measured in vitro by performing an elution assay. An elution assay measures the drug elution profile of a coated medical device. Different elution media can be used that provide desired rates of drug elution. For example, an elution medium such as SDS can be selected to quickly dissolve a hydrophobic therapeutic agent in the coating, for example to measure the total amount of therapeutic agent. Alternatively, an elution medium such as porcine serum can be selected to gradually dissolve the hydrophobic therapeutic agent over a much longer period time, for example to measure the rate of release of the therapeutic agent. In one embodiment, the elution profile of a therapeutic agent may be obtained in vitro by contacting the medical device with a modified porcine elution medium prepared by adding 0.104 mL of a 6.0 g/L Heparin solution to porcine serum and adjusting the pH to 5.6±0.3 using a 20% v/v aqueous solution of acetic acid. This modified procine serum elution medium provides for the gradual release of the therapeutic agent at a rate that is similar to blood. Alternatively, other elution media can be used to more rapidly dissolve the therapeutic agent.

For therapeutic agents that are soluble in a cyclodextrin solution, such as taxane agents, elution profiles may also be obtained by contacting a coated medical device with an elution medium comprising a cyclodextrin. A cyclodextrin is a cyclic oligosaccharide formed from covalently-linked glucopyranose rings defining an internal cavity. The diameter of the internal axial cavity of cyclodextrins increases with the number of glucopyranose units in the ring. The size of the glucopyranose ring can be selected to provide an axial cavity selected to match the molecular dimensions of a taxane agent. The cyclodextrin is preferably a modified β-cyclodextrin, such as Heptakis-(2,6-di-O-methyl)-β-cyclodextrin (HCD). Suitable cyclodextrin molecules include other β-cyclodextrin molecules, as well as γ-cyclodextrin structures.

For example, solvated solid forms of taxane agents, such as dihydrate paclitaxel, typically have desirably sustained elution rates, as exemplified by a solubility of less than about 40 wt % after 24 hours in porcine serum at 37° C., or having a solubility of less than 20% wt. after 1 hour in a 0.5% aqueous solution of Heptakis-(2,6-di-O-methyl)-β-cyclodextrin at 25° C. In contrast, non-solvated solid forms of taxane agents, including the amorphous and anhydrous solid forms, typically elute more rapidly, as evidenced by a solubility of greater than 50% after 24 hours in porcine serum at 37° C. or a solubility of greater than 50% wt. after 1 hour in a 0.5% aqueous solution of Heptakis-(2,6-di-O-methyl)-β-cyclodextrin at 25° C.

The elution medium comprising a cyclodextrin can dissolve a taxane agent so as to elute the taxane agent from a medical device coating over a desired time interval, typically about 24 hours or less. Preferably, the cyclodextrin elution medium is formulated to provide distinguishable elution rates for different coating configurations, such as different solid forms of a taxane agent in the coating, or different types or amounts of polymers incorporated with the taxane agent within a coating.

An elution medium comprising a suitable cyclodextrin may be useful in providing an elution profile indicative of the composition or configuration of a medical device coating comprising a taxane agent, and useful to provide lot release data pertaining to the coating of the medical device. For example, the elution profile of a medical device coating formed from a solvated solid form of a taxane agent measured in a cyclodextrin elution medium typically provides a distinguishably slower rate of elution than a medical device coating formed from an amorphous solid form of the taxane agent in the same elution medium. Similarly, the elution profile of a coating comprising both a taxane agent and differing amounts of a biodegradable elastomer, such as poly(lactic acid), can be distinguished based on the elution profiles in a cyclodextrin elution medium. Obtaining an elution profile by contacting a taxane-coated medical device with an elution medium comprising a suitable cyclodextrin provides a method for obtaining lot release data indicative of differences in coating configuration that are distinguishable based on solubility of the taxane agent in the cyclodextrin.

Medical Devices

The coatings may be applied to implantable or insertable medical devices of various configurations and functions. Typical subjects (also referred to herein as "patients") are vertebrate subjects (i.e., members of the subphylum cordata), including, mammals such as cattle, sheep, pigs, goats, horses, dogs, cats and humans. Typical sites for placement of the medical devices include the coronary and peripheral vasculature (collectively referred to herein as the vasculature), heart, esophagus, trachea, colon, gastrointestinal tract, biliary tract, urinary tract, bladder, prostate, brain and surgical sites. Where the medical device is inserted into the vasculature, for example, the therapeutic agent may be released to a blood vessel wall adjacent the device, and may also be released to downstream vascular tissue as well.

The medical device of the invention may be any device that is introduced temporarily or permanently into the body for the prophylaxis or therapy of a medical condition. For example, such medical devices may include, but are not limited to, stents, stent grafts, vascular grafts, catheters, guide wires, balloons, filters (e.g. vena cava filters), cerebral aneurysm filler coils, intraluminal paving systems, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves (e.g. venous valves), abdominal aortic aneurysm (AAA) grafts, embolic coils, various types of dressings, bone substitutes, intraluminal devices, vascular supports, or other known biocompatible devices.

In general, intraluminal stents for use in connection with the present invention typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube). Examples of intraluminal stents include endovascular, biliary, tracheal, gastrointestinal, urethral, ureteral, esophageal and coronary vascular stents. The intraluminal stents of the present invention may be, for example, balloon-expandable or self-expandable. Thus, although certain embodiments of the present invention will be described herein with reference to vascular stents, the present invention is applicable to other medical devices, including other types of stents.

In one embodiment of the present invention, the medical device comprises an intraluminal stent. The stent may be self-expanding or balloon-expandable and may be a bifurcated stent, a stent configured for any blood vessel including a coronary arteries and peripheral arteries (e.g., renal, Superficial Femoral, Carotid, and the like), a urethral stent, a biliary stent, a tracheal stent, a gastrointestinal stent, or an esophageal stent.

The stent or other medical device of the invention may be made of one or more suitable biocompatible materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber.

Methods of Treatment

A method of treatment according to the present invention may include inserting into a patient a coated medical device having any of the configurations described above. For example, when the medical device is a stent coated by the coating methods described above, the method of treatment involves implanting the stent into the vascular system of a patient and allowing the therapeutic agent(s) to be released from the stent in a controlled manner, as shown by the drug elution profile of the coated stent.

In one preferred embodiment, the coated medical devices are implanted to treat peripheral vascular disease, for example by implanting the coated medical device in a peripheral artery. Peripheral vascular disease (PVD) is a common condition with variable morbidity affecting mostly men and women older than 50 years. Peripheral vascular disease of the lower extremities comprise a clinical spectrum that goes from asymptomatic patients, to patients with chronic critical limb ischemia (CLI) that might result in amputation and limb loss. Critical limb ischemia is a persistent and relentless problem that severely impairs the patient functional status and quality of life, and is associated with an increased cardiovascular mortality and morbidity. It can present acutely (i.e. distal embolization, external compression, acute thrombosis, etc.) or, in the majority of cases, as chronic CLI. Based on incidence rates extrapolated to today's increasingly aging population, PVD affects as many as 10 million people in the United States (Becker G J, McClenny T E, Kovacs M E, et al., "The importance of increasing public and physician awareness of peripheral arterial disease," J Vasc Interv Radiol., 13(1):7-11 (January 2002)). As the population ages, the family physician will be faced with increasing numbers of patients complaining of symptoms of lower extremity PVD. Nearly one in four of the approximately 60,000 people screened annually through Legs for Life, a nationwide screening program, are determined to be at moderate to high risk of lower extremity PVD and are referred to their primary care physicians for diagnosis (data collected by the Society of Cardiovascular and Interventional Radiology) (Becker G J, McClenny T E, Kovacs M E, et al., "The importance of increasing public and physician awareness of peripheral arterial disease," J Vasc Interv Radiol., 13(1):7-11 (January 2002)).

Chronic critical limb ischemia is defined not only by the clinical presentation but also by an objective measurement of impaired blood flow. Criteria for diagnosis include either one of the following (1) more than two weeks of recurrent foot pain at rest that requires regular use of analgesics and is associated with an ankle systolic pressure of 50 mm Hg or less, or a toe systolic pressure of 30 mm Hg or less, or (2) a nonhealing wound or gangrene of the foot or toes, with similar hemodynamic measurements. The hemodynamic parameters may be less reliable in patients with diabetes because arterial wall calcification can impair compression by a blood pressure cuff and produce systolic pressure measurements that are greater than the actual levels. Ischemic rest pain is classically described as a burning pain in the ball of the foot and toes that is worse at night when the patient is in bed. The pain is exacerbated by the recumbent position because of the loss of gravity-assisted flow to the foot. Ischemic rest pain is located in the foot, where tissue is farthest from the heart and distal to the arterial occlusions. Patients with ischemic rest pain often need to dangle their legs over the side of the bed or sleep in a recliner to regain gravity-augmented blood flow and relieve the pain. Patients who keep their legs in a dependent position for comfort often present with considerable edema of the feet and ankles. Nonhealing wounds are usually found in areas of foot trauma caused by improperly fitting shoes or an injury. A wound is generally considered to be nonhealing if it fails to respond to a four- to 12-week trial of conservative therapy such as regular dressing changes, avoidance of trauma, treatment of infection and debridement of necrotic tissue. Gangrene is usually found on the toes. It develops when the blood supply is so low that spontaneous necrosis occurs in the most poorly perfused tissues.

Treatment and prognosis of peripheral vascular disease can be influenced by lesion and patient characteristics, such as the site of the lesion, type of lesion (stenosis or occlusion, lesion length), arterial runoff, and clinical manifestation (Dormandy J A, Rutherford R B. Management of peripheral arterial disease (PAD): TASC Working Group. J Vasc Surg 2000; 31 (1 pt 2):S103-S106). Estimates of the 5-year patency rate of balloon dilation for femoropopliteal arterial disease range from as low as 12% in patients with an occlusion and critical ischemia to 68% in patients with a stenosis and claudication (Hunink M G M, Wong J B, Donaldson M C, Meyerovitz M F, Harrington D P. Patency results of percutaneous and surgical revascularization for femoropopliteal arterial disease. Med Decis Making 1994; 14:71-81). Bypass surgery for femoropopliteal arterial disease has been associated not only with higher long-term patency rates but also with a higher procedural morbidity, mortality, and a longer hospital stay (Hunink M G M, Wong J B, Donaldson M C, Meyerovitz M F, de Vries J A, Harrington D P. Revascularization for femoropopliteal disease. A decision and cost-effectiveness analysis. JAMA 1995; 274:165-171).

Methods of treating peripheral vascular disease, including critical limb ischemia, preferably comprise the endovascular implantation of one or more coated medical devices provided herein. Atherosclerosis underlies many cases of peripheral vascular disease, as narrowed vessels that cannot supply sufficient blood flow to exercising leg muscles may cause claudication, which is brought on by exercise and relieved by rest. As vessel narrowing increases, critical limb ischemia (CLI) can develop when the blood flow does not meet the metabolic demands of tissue at rest. While critical limb ischemia may be due to an acute condition such as an embolus or thrombosis, most cases are the progressive result of a chronic condition, most commonly atherosclerosis. The development of chronic critical limb ischemia usually requires multiple sites of arterial obstruction that severely reduce blood flow to the tissues. Critical tissue ischemia can be manifested clinically as rest pain, nonhealing wounds (because of the increased metabolic requirements of wound healing) or tissue necrosis (gangrene).

The coated medical device can be implanted in any suitable body vessel. The configuration of the implantable frame can be selected based on the desired site of implantation. For example, for implantation in the superficial artery, popliteal artery or tibial artery, frame designs with increased resistance to crush may be desired. For implantation in the renal or iliac arteries, frame designs with suitable levels of radial force and flexibility may be desired. Preferably, a coated vascular stent is implanted in a non-coronary peripheral artery, such as the iliac or renal arteries.

In one embodiment, a medical device comprising a balloon-expandable frame portion coated with a therapeutic agent covered by a layer of biodegradable elastomer polymer can be endoluminally delivered to a point of treatment within an infrapopliteal artery, such as the tibial or peroneal artery or in the iliac artery, to treat CLI. For treating focal disease conditions, coated balloon-expandable medical devices can comprise an expandable frame attached to a coating. The frame can be also be formed from a bioabsorbable material, or comprise a coating of bioabsorbable material over at least a portion of the frame. The frame can be configured to include a barb or other means of securing the medical device to the wall of a body vessel upon implantation.

In another embodiment, a coated medical device can be a self-expanding device such as a coated NITINOL stent configured to provide a desirable amount of outward radial force to secure the medical device within the body vessel. The medical device can be preferably implanted within the tibial arteries for treatment of CLI. For instance, the coated medical device can be configured as a vascular stent having a self-expanding support frame formed from a superelastic self-expanding nickel-titanium alloy coated with a metallic bioabsorbable material and attached to a graft material. A self-expanding frame can be used when the body vessel to be stented extends into the distal popliteal segment. The selection of the type of implantable frame can also be informed by the possibility of external compression of an implant site within a body vessel during flexion of the leg.

Methods for delivering a medical device as described herein to any suitable body vessel are also provided, such as a vein, artery, biliary duct, ureteral vessel, body passage or portion of the alimentary canal.

Although exemplary embodiments of the invention have been described with respect to the treatment of complications such as restenosis following an angioplasty procedure, the local delivery of therapeutic agents may be used to treat a wide variety of conditions using any number of medical devices. For example, other medical devices that often fail due to tissue ingrowth or accumulation of proteinaceous material in, on, or around the device may also benefit from the present invention. Such devices may include, but are not limited to, intraocular lenses, shunts for hydrocephalus, dialysis grafts, colostomy bag attachment devices, ear drainage tubes, leads for pace makers, and implantable defibrillators.

A consensus document has been assembled by clinical, academic, and industrial investigators engaged in preclinical interventional device evaluation to set forth standards for evaluating drug-eluting stents such as those contemplated by the present invention. See "Drug-Eluting Stents in Preclinical Studies—Recommended Evaluation From a Consensus Group" by Schwartz and Edelman (available at "http://www.circulationaha.org") (incorporated herein by reference).

Methods for delivering a medical device as described herein to any suitable body vessel are also provided, such as a vein, artery, biliary duct, ureteral vessel, body passage or portion of the alimentary canal.

While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

The invention includes other embodiments within the scope of the claims, and variations of all embodiments, and is limited only by the claims made by the Applicants.

EXAMPLES

In the following examples, the equipment and reagents specified below were used:

TABLE 3

Reagents and Equipment

| Equipment Name | Manufacturer | Manufacturer ID | Vendor |
|---|---|---|---|
| 1 µg Balance | Mettler | AX 26 | VWR |
| 10 µg Balance | Mettler | AX 105 DR | VWR |
| Top Loading Balance | Ohaus | GT 4100 (not avail.) | VWR |
| Inline Spectrometer | Agilent | 8453 | Agilent |
| Chemstation | Agilent | Version A. 10.01 | Agilent |
| Coating Spectrometer 1 | Perkin Elmer | Lambda 14 P | Perkin Elmer |
| Coating Spectrometer 2 | Perkin Elmer | Lambda 45 | Perkin Elmer |
| UV Winlab | Perkin Elmer | Version 5.1 | Perkin Elmer |
| Cuvettes | Perkin Elmer | B0631077 | VWR |
| Electrostatic Coater | Terronics | Custom | Terronics |
| MED Spray Gun/Badger | Badger | Model 200 | Ding-A-Ling |
| Cook Incorporated Spray Gun | EFD | 780S-SS | EFD |
| Cook Incorporated Spray Controller | EFD | Valvemate 7040 | EFD |
| Microscope | Leica | MZ-16 | Nuhsbaum Inc. |
| Image Pro Plus | MediaCybernetics | Version 5.1 | Media Cybernetics |

TABLE 3-continued

Reagents and Equipment

| Equipment Name | Manufacturer | Manufacturer ID | Vendor |
|---|---|---|---|
| Microsoft Office | Microsoft | Version 2003 | New Egg |
| Stopwatch | Private Label | n/a | VWR |
| Glassware | Kimball | Various | VWR |
| Ethanol | Aaper | E 200 PP | Aaper |
| Methanol | Sigma | M 3641 | Sigma |
| Dichloromethane | Sigma | 15,479-2 | Sigma |
| Water | Ricca Chemical | 9150-5 | VWR |

Example 1

Preparation of Amorphous, Anhydrous and Dihydrate Paclitaxel

Bulk samples of amorphous, anhydrous and dihydrate paclitaxel solid forms are prepared by the methods described below. These preparations were reproduced based on Jeong Hoon Lee et al., "Preparation and Characterization of Solvent Induced Dihydrate, Anhydrous and Amorphous Paclitaxel," *Bull. Korean Chem. Soc.* v. 22, no. 8, pp. 925-928 (2001).

Samples of bulk amorphous paclitaxel are prepared as follows: 1.01 g of paclitaxel (Phytogen Life Sciences) was dissolved in 5 mL dichloromethane (Mallinckrodt) while agitating to form a paclitaxel solution; the paclitaxel solution is left open to air at about 23° C. for about 10 hours to permit evaporation of the dichloromethane and formation of amorphous paclitaxel. The melting temperature of the amorphous paclitaxel is 209-215° C.

Samples of bulk anhydrous paclitaxel are prepared as follows: 1.06 g of paclitaxel (Phytogen Life Sciences) were dissolved in 40 mL methanol (Sigma Aldrich, 99.93% HPLC Grade) while sonicating the container and inversion of the container to form a paclitaxel solution; about 2 mL of hexane (Sigma Aldrich) is added to the paclitaxel solution, and the solution is placed in a freezer at about −20° C. overnight (approximately 10 hours) to form anhydrous crystalline paclitaxel. The melting temperature of the anhydrous paclitaxel is 190-210° C.

Samples of dihydrate paclitaxel are prepared as follows: 1.09 g paclitaxel (Phytogen Life Sciences) are dissolved in 25 mL methanol while sonicating the container to form a paclitaxel solution; about 5 mL of water is added to the paclitaxel solution; and the sample placed in a freezer at about −20° C. overnight to form dihydrate crystals. The melting temperature of the dihydrate crystal is 209-215° C. Subsequently, the sample is sealed under vacuum to 0.025 torr for 2.5 hours to remove residual solvent. Dihydrate paclitaxel samples are also prepared as follows: 50.08 g paclitaxel (Phytogen Life Sciences) is dissolved in 1.1 L methanol to form a solution; 275 mL water is subsequently added to the methanol solution in a drop-wise fashion to form a precipitate that is refrigerated at about −20° C. overnight (about 10 hours); the resulting solid precipitate is filtered, dissolved in 1500 mL methanol and 375 mL water and is subsequently added in a drop-wise fashion; the resulting crystals are recrystallized a third time using 1200 mL methanol with 300 mL water; and the resulting dihydrate crystals collected.

Example 2

Ultraviolet (UV) Spectra of Bulk Paclitaxel Samples

The three solid samples prepared in Example 1 (amorphous, dihydrate and anhydrous paclitaxel) are dissolved in ethanol to form spray sample solutions. The ultraviolet spectra of each of the three samples are taken (Agilent In-Line UV Spectrophotometer), to obtain three spectra that are indistinguishable from the spectrum 100 shown in FIG. 3A. The spectra all include a peak at 227 nm indicative of the taxane core structure in the paclitaxel, indicating that the paclitaxel solid forms of Example 1 are not distinguishable from each other based on UV spectra of the paclitaxel in solution.

Example 3

Infrared Spectra of Bulk Paclitaxel Samples

FTIR Infrared spectra each of the samples prepared in Example 1 were obtained following procedure: a pellet of KBr was made by grinding the paclitaxel crystal with KBr using a mortar and pestle at room temperature (about 23° C.); the resulting solid was placed under vacuum to remove residual methanol solvent (0.025 mmHg); and a spectra was recorded of the paclitaxel analyte. Representative spectra of each solid form of paclitaxel are provided in FIGS. 3B-3D, as discussed above. Infrared spectra may also be obtained using Attenuated Total Reflection Infrared (ATR-IR) from a coating or a small sample of a solid taxane sample from a coating. One suitable ATR-IR apparatus is the PerkinElmer Horizontal ATR model L1200361.

Example 4

Ultrasonic Spray Coating of Stents with Paclitaxel

Stents with coatings consisting of paclitaxel coatings including both the dihydrate solid form and in the amorphous solid forms of paclitaxel are prepared by spray coating a solution comprising paclitaxel, methanol and water. A paclitaxel solution in methanol and water is prepared. Specifically, a 1.74 mM paclitaxel solution is prepared in 68% methanol by dissolving 7.43 mg of paclitaxel in 5 mL of previously made solution of 68% methanol 32% water. The solution is sprayed from an ultrasonic spray gun (Sono-tek Model 06-04372) in a glove box. Before spraying, the glove box is purged with nitrogen at 20 psi for 15 minutes. The atmosphere in the glove box is adjusted until the oxygen meter reads a constant 200 ppm within the glove box. The heat in the glovebox is set to 31° C. (88° F.), the air shroud to 2.0 psi and the ultrasonic power to 1.0 W. The paclitaxel solution is loaded into a syringe and place on the syringe pump in the ultrasonic coating apparatus and a bare metal stent (6×20 ZILVER, Cook Inc., Bloomington, Ind.) is mounted on a mandrel aligned with the spray nozzle. The solution is sprayed onto a stent using a 60 kHz nozzle at a flow rate of 0.03 mL/min, a coating velocity of 0.025 in/sec, a nozzle power of 1.0 W, a process gas pressure of 2.0 psi, and a distance from the nozzle to the stent of about 12 mm, while rotating the stent with an axial rotation rate of 60 rpm. Only the abluminal surface of the stent is coated.

Example 5

Post-Deposition Conditioning of Paclitaxel-Coated Stents

Paclitaxel-coated stents may be prepared by spraying the abluminal surface of a medical device with a solution of paclitaxel in a suitably volatile solvent, such as ethanol. The coating preferably contains enough paclitaxel in the amorphous (clear) solid state to provide a suitable level of durability. The coating may be conditioned by, in this example, raising the temperature to between about 35° C. and 50° C. (or higher) and a relative humidity level of about 75%-100% for a period of at least about 5 hours, and preferably about 12-15 hours or longer.

In this example, a substantially visually clear paclitaxel coating is applied to the abluminal surface of a 6×20 mm ZILVER stent (Cook Incorporated, Bloomington, Ind.) by spraying a solution consisting of paclitaxel dissolved in ethanol onto the abluminal surface of the stent. The spray gun is passed over the stent for multiple passes until a desired dose of paclitaxel is coated on the abluminal surface of the stent. For example, the paclitaxel coatings may be spray deposited until the coatings contain a dose of about up to about 4 µg of the paclitaxel per $mm^2$ of the abluminal surface area of the stent, depending on the number of applications by the spray gun. The spray coating conditions are selected to evaporate the ethanol solvent during the spraying process, or in combination with a step of drying the sprayed stents. The resulting coating consisted of the paclitaxel on the abluminal side of the stent one or more solid forms, including the amorphous solid form.

The solid form(s) of paclitaxel present in the coating may be identified by visual inspection and solubility of the coating in an elution medium described herein. Elution medium such as an aqueous solution of cyclodextrin may be contacted with the paclitaxel coating, and the concentration of paclitaxel in the elution medium can be monitored as a function of time using UV spectrophotometry. A clear paclitaxel coating is indicative of an amorphous solid form, while a white or cloudy coating is indicative of a solvated (e.g., dihydrate) solid form of paclitaxel. The dihydrate solid form is less soluble in an aqueous cyclodextrin elution medium than the amorphous solid form. Accordingly, a paclitaxel coating having a higher percentage of the dihydrate solid form typically will have a slower rate of elution from the coating than a coating with a higher percentage of the amorphous solid form.

By coating multiple stents using comparable or identical coating methods, the composition of the coatings may be estimated by eluting one of the coatings in a suitable elution medium as an estimate of the coating composition of other stents coated using comparable or identical coating methods. One representative coated stent can be tested to determine the paclitaxel solid forms present in the other coatings. The presence of both dihydrate and amorphous solid forms may be identified by the difference in solubility properties of the two solid forms: contacting the coating with a porcine serum elution medium can elute the amorphous solid form, while subsequent contact with sodium dodecyl sulfate can elute the remaining paclitaxel. The elution rate can be monitored by UV-detection of the elution medium after contact with the paclitaxel coating. Another representative coated stent can be weighed before and after crimping, and the percentage of coating weight loss can be measured. Typical coating weight loss during crimping is about 6%.

The coated stent was crimped onto the distal portion of a delivery catheter and then conditioned by maintaining the paclitaxel coated stent at a temperature to about 120° F. (48° C.) at a relative humidity to about 100% for a period of about 13 hours. After the conditioning process, areas of the paclitaxel coating that were substantially clear (transparent) became white and clouded, indicated formation of dihydrate paclitaxel. Subsequent elution tests of the coating indicated an increase in the amount of dihydrate paclitaxel in the coating relative to other comparable paclitaxel stent coatings that were not conditioned.

After conditioning, a coated stent can be tested by dissolution in any suitable elution medium, such as aqueous HCD solution followed by sodium dodecyl sulfate or ethanol to identify the solid forms present in the conditioned coating. The weight percentage of the dihydrate paclitaxel solid form is higher in the conditioned coating than in the coating before conditioning. The dihydrate paclitaxel is preferably up to about 75% of the coating weight. Another conditioned stent can be weighed before and after crimping, and the percentage of coating weight loss measured. Typical values for coating weight loss of a conditioned stent are expected to be less than 6%, for example about 3-5%.

Example 6

Single Layer of PLA Over Single Layer of Paclitaxel on a Stent Using Ultrasonic Deposition Method The Zilver® stents are coated with either approximately 3 µg/$mm^2$ (approximately 200 µg) of amorphous paclitaxel or with the same amount of a composition including 50-60% dihydrate paclitaxel. Coating is performed using an ultrasonic nozzle.

Once the stents are coated with the paclitaxel, 0.5 µg/$mm^2$ (approximately 40 µg) of PLA is applied by dissolving 2 to 4 g/L PLA in acetone. The solution is then applied by using the ultrasonic nozzle. The solution is loaded into a 10.0 mL syringe, which is mounted onto a syringe pump and connected to a tube that carries the solution to a spray head. The syringe pump was then used to purge the air from the solution line and prime the line and spray nozzle with the solution. The ultrasonic nozzle is arranged such that excitation of the piezoelectric crystals generates a transverse standing wave along the length of the nozzle. So the solution introduced onto the atomizing surface absorbs some of the vibrational energy, setting up wave motion in the liquid. For the liquid to atomize, the vibrational amplitude of the atomizing surface must be carefully controlled. The coating chamber is purged with nitrogen to displace any oxygen in the system. The coating method is created and the system is set-up using the corresponding parameters. After that, one end of the stent is slipped onto a mandrel and half of the stent is coated. The nozzle is manually aligned to the tip of the stent and the middle of the stent. These position numbers are used for the coating program when the syringe pump is actually activated. The stent is turned over and the other half is coated. During the process, the stent is kept at ambient temperature and in a closed chamber.

TABLE 4

Process Parameters for Ultrasonic Coating

| Flow rate (mL/min) | Coating velocity (in/sec) | Rotation Speed (rpm) | Nozzle Power (watts) | Process Gas (psi) | Distance (mm) |
|---|---|---|---|---|---|
| 0.01-2 | 0.005-0.5 | 30-150 | 0.9-1.2 | 0.1-2.5 | 1-25 |

TABLE 5

| PTX | PLA | | |
|---|---|---|---|
| | 75 +/− 112 µg PLA (0.94 µg/mm²) | 134 +/− 10 µg PLA (1.6 µg/mm²) | 170 +/− 26 µg PLA (2.0 µg/mm²) |
| 5.3 +/− 0.3 µg PTX (0.06 µg/mm²) | 70% | | 42% |
| 7.8 +/− 0.4 µg PTX (0.1 µg/mm²) | | 54% | |
| 23 +/− 2.5 µg PTX (0.3 µg/mm²) | | 48% | |
| 69 +/− 4.2 µg PTX (1.0 µg/mm²) | 90% | | 72% |

Example 7

Elution of Paclitaxel-Coated Stents in HCD and SDS

ZILVER (Cook Inc., Bloomington, Ind.) stents with coatings consisting of paclitaxel in both the amorphous form and containing approximately 50-60% dihydrate solid form were prepared using a procedure based on that described in Example 4. The stents were then over coated with PLA using an acetone solvent.

Figure 4:
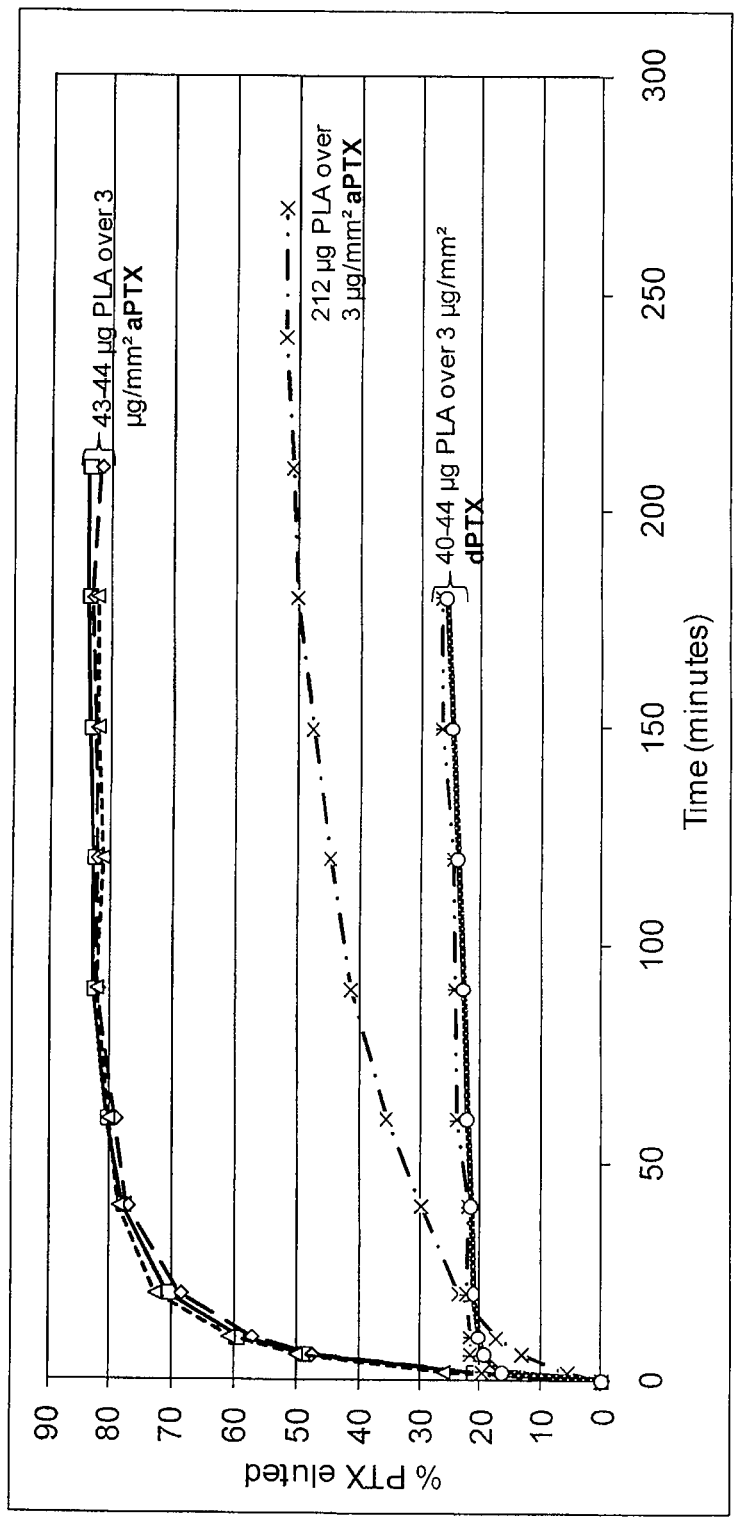
FIG. 4 shows paclitaxel elution profiles in HCD.

The elution of paclitaxel from the stents was determined in two elution media: 5% Heptakis-(2,6-di-O-methyl)-β-cyclodextrin (HCD) and 1% sodium dodecyl sulfate (SDS). Elution profiles were determined by measuring for UV absorbance of eluted paclitaxel at 227 nm and correlating this to paclitaxel test solutions. FIG. 4 shows elution profiles obtained in 5% HCD. Stents coated with 3 µg/mm² amorphous paclitaxel and an overcoat of 43-44 µg of PLA released paclitaxel quicker than did those stents containing the dihydrate form.

FIG. 4 also shows an elution profile from a stent coated with 3 µg/mm² of the amorphous form of paclitaxel and overcoated with a greater amount of PLA (212 µg of PLA). Although increasing the weight of PLA in the overcoat appears to reduce the release for periods up to about 10 minutes. For longer times, the release of paclitaxel from this stent is more rapid that from the stents containing the dihydrate form.

FIG. 5 shows elution obtained in 1% SDS. Here, a stent having the dihydrate form of paclitaxel and overcoated with PLA reached 80% elution about 5 times more slowly than a stent coated with a similar weight of the amorphous form of paclitaxel and a similar weight of PLA.

We claim:

1. A coated implantable medical device comprising a coating configured to release a taxane agent adhered to a surface of the medical device, the coating comprising:
   a first layer comprising a taxane agent, wherein the taxane agent is paclitaxel comprising at least one of amorphous paclitaxel and anhydrous paclitaxel and at least 40% dihydrate paclitaxel; and
   a second layer positioned over the first layer and comprising biodegradable elastomer, the biodegradable elastomer having a molecular weight of 50-500 kDa, and being present in an amount between 1 and 20 times the weight of the therapeutic agent in the first layer.

2. The coated implantable medical device of claim 1, wherein the biodegradable elastomer is poly(lactic acid).

3. The coated implantable medical device of claim 1, wherein the taxane agent comprises at least 60% dihydrate paclitaxel.

4. The coated implantable medical device of claim 1 comprising a radially-expandable vascular stent.

5. A coated implantable medical device comprising a coating configured to release a taxane agent adhered to a surface of the medical device, the coating comprising:
   a first layer comprising a taxane agent, wherein the taxane agent is paclitaxel comprising at least one of amorphous paclitaxel and anhydrous paclitaxel and at least 20% dihydrate paclitaxel; and
   a second layer positioned over the first layer and comprising a biodegradable elastomer, the biodegradable elastomer being present in an amount between 1 and 20 times the weight of the taxane agent in the first layer.

6. The coated implantable medical device of claim 5, wherein the dihydrate paclitaxel comprises at least 40% of the taxane agent.

7. The coated implantable medical device of claim 6, wherein the dihydrate paclitaxel comprises at least 60% of the taxane agent.

8. The coated implantable medical device of claim 5, wherein the biodegradable elastomer is poly(lactic acid).

9. A coated implantable medical device comprising a coating configured to release a taxane agent adhered to a surface of the medical device, the coating comprising:
   a first layer comprising paclitaxel in a first solid form and a second solid form, wherein the first solid form is dihydrate paclitaxel, wherein the second taxane solid form is selected from the group consisting of amorphous paclitaxel and anhydrous paclitaxel, and wherein at least 10% of the paclitaxel is in the first solid form; and
   a second layer positioned over the first layer and comprising a biodegradable elastomer, the biodegradable elastomer having a molecular weight of 50-500 kDa, and being present in an amount between 1 and 20 times the weight of the therapeutic agent in the first layer.

10. The coated implantable medical device of claim 9, wherein the biodegradable elastomer is poly(lactic acid).

11. The coated implantable medical device of claim 9, wherein the coated implantable medical device is a balloon.

12. The coated implantable medical device of claim 9, wherein the paclitaxel comprises at least 20% dihydrate paclitaxel.

13. The coated implantable medical device of claim 12, wherein the paclitaxel comprises at least 40% dihydrate paclitaxel.

14. The coated implantable medical device of claim 13, wherein the paclitaxel comprises at least 60% dihydrate paclitaxel.

15. The coated implantable medical device of claim 14, wherein the paclitacel comprises at least 80% dihydrate paclitaxel.

16. The coated implantable medical device of claim 1, wherein the coated implantable medical device is a balloon.

17. The coated implantable medical device of claim 16, wherein the balloon is for use in the peripheral arteries.

18. The coated implantable medical device of claim 17, wherein the balloon is for use in the superficial femoral artery.

19. The coated implantable medical device of claim 1, wherein the coated implantable medical device is a radially-expandable vascular stent for use in the peripheral arteries.

20. The coated implantable medical device of claim 19, wherein the radially-expandable vascular stent is for use in the superficial femoral artery.

* * * * *